United States Patent [19]
Sessler et al.

[11] Patent Number: 5,594,136
[45] Date of Patent: Jan. 14, 1997

[54] TEXAPHYRIN SOLID SUPPORTS AND DEVICES

[75] Inventors: Jonathan L. Sessler; Brent L. Iverson; Vladimir Král, all of Austin, Tex.; Richard E. Thomas, Chesapeake, Va.; Darren Magda, Cupertino, Calif.; Daniel A. Smith, Goshen, Ind.

[73] Assignees: Pharmacyclics, Inc., Sunnyvale, Calif.; Board of Regents, The University of Texas, Austin, Tex.

[21] Appl. No.: 433,573

[22] Filed: May 3, 1995

Related U.S. Application Data

[63] Continuation-in-part of Ser. No. 236,218, Apr. 28, 1994, which is a continuation-in-part of Ser. No. 964,607, Oct. 21, 1992, Pat. No. 5,457,195, which is a continuation-in-part of Ser. No. 454,298, Dec. 21, 1989, Pat. No. 5,159,065.

[51] Int. Cl.$^6$ .................... C07D 487/22; C07F 15/02
[52] U.S. Cl. .................... 540/472; 540/145; 540/474; 404/9.322; 504/15; 504/11; 504/14; 504/16
[58] Field of Search .................... 540/472, 474, 540/145; 424/9.322; 534/11, 14, 15, 16

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,120,411 | 6/1992 | Sessler et al. | 204/157.15 |
| 5,141,911 | 8/1992 | Meunier et al. | 502/159 |
| 5,159,065 | 10/1992 | Sessler et al. | 534/15 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |
| 5,457,195 | 10/1995 | Sessler et al. | 540/472 |

FOREIGN PATENT DOCUMENTS

| | | |
|---|---|---|
| 0111418 | 6/1984 | European Pat. Off. |
| 0196515 | 10/1986 | European Pat. Off. |
| 0233701A2 | 8/1987 | European Pat. Off. |
| 90/01208 | 8/1990 | WIPO |
| WO90/10633 | 9/1990 | WIPO |
| 91/19730 | 12/1991 | WIPO |
| 92/01781 | 2/1992 | WIPO |
| WO93/14093 | 7/1993 | WIPO |
| WO94/09003 | 4/1994 | WIPO |
| WO94/29316 | 12/1994 | WIPO |

OTHER PUBLICATIONS

Abid et al., "Lanthanide Complexes of Some Macrocyclic Schiff Bases Derived from Pyridine–2, 6–dicarboxaldehyde and $\alpha,\omega$–Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating 'Accordian'Tetrapyrrole Macrocycle", *Tetrahedron Lett.*, 25: 3269–3270, 1984.

Ansell, "X–Ray Crystal Structure of the Pentagonal Bipyramidal Nickel (11) Complex $[Ni^{11}(L)(H_2O)_2](BF_4)_2$ and the Selective Stabilisation of the Nickel(1) Oxidation State by a Quinquedentate Macrocyclic Ligand", *J. Chem. Soc., Chem. Commun.* pp. 546–547, 1982.

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a *meso*–Thiaphlorin", *J. Chem. Soc., Chem. Commun.* pp. 807–809, 1970.

Broadhurst et al., "18–and 22–$\pi$–Electron Macrocycles Containing Furan, Pyrrole, and Thiophen Rings", *J. Chem. Soc., Chem. Commun.* pp. 1480–1482, 1969.

Broadhurst et al., "New Macrocyclic Aromatic Systems Related to Porphins", *J. Chem. Soc., Chem. Commun.* pp. 23–24, 1969.

Broadhurst et al., "The Synthesis of 22 $\pi$–Electron Macrocycles. Sapphyrins and Related Compounds", *J. Chem. Soc. Perkin Trans.*, 1:2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97: 4519–4527, 1975.

(List continued on next page.)

Primary Examiner—Mukund J. Shah
Assistant Examiner—Pavanaram K. Sripada
Attorney, Agent, or Firm—Arnold, White & Durkee

[57] ABSTRACT

The present invention provides various novel matrix-supported texaphyrins in which a polymeric or solid matrix is covalently modified by the addition of one or more texaphyrins or texaphyrin derivatives. Described are methods of making various polymer-supported texaphyrins, including texaphyrin chromatographic supports, and devices such as catheters, as may be used, for example, in the separation of neutral and anionic species and in applications concerning phosphate ester hydrolysis, other catalytic schemes, MRI, and PDT.

44 Claims, No Drawings

OTHER PUBLICATIONS

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Gossauer, "Syntheses of Some Unusual Polypyrrole Macrocycles", *Bull. Soc. Chim. Belg.*, 92:793–795, (1983).

Knubel et al., "Biometic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the 'Superphthalocyanine' Dioxocyclopentakis (1–iminoisoindolinato) uranium (VI) and Its Derivatives", *J. Am. Chem. Soc.*, 100: 1695–1705, 1978.

Rexhausen et al., "The Synthesis of a New 22 π–Electron Macrocycle: Pentaphyrin", *J. Chem. Soc., Chem. Commun.*, p. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate 'Porphyrin–Like' Lignads", *Comm. Inorg. Chem.*, 7:333–350, 1988.

Sessler et al., "An 'Expanded Porphyrin': The Synthesis and Structure of a New Aromatic Pentadentate Ligand", *J. Am. Chem. Soc.*, 110:5586–5588, 1988.

Tweedle et al., "Principles of Contrast–Enhanced MRI", in 'Magnetic Resonance Imaging,' 2nd ed. Partain, et al, Eds., W. B. Saunders: Philadelphia, vol. I (1988) 793–809.

Vogel et al., "Porphycene—a Novel Porphin Isomer", *Angew. Chem., Int. Ed. Engl.*, 25:257–259, 1986.

Vogel et al., "2,7,12,17–Tetrapopylporphycene–Counterpart of Octaethylporphyrin in the Porphycene Series", *Agnew. Chem. , Int. Ed. Engl.*, 26:928–931, 1987.

Sessler et al., "A Warter–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin : Solution and X-ray Structural Studies",*Inorg. Chem..*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadoinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin––type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin ': A Novel 22 π–Electron Aromatic Pentadentate Macrocyclic Ligand", *ACS meeting*,Los Angeles, Sept. 1988.

Sessler and Burrell, "Expanded Porphyrins, " *Topics in Current Chemistry*, 161: 180–273, 1991.

Sessler et al., "Synthesis and Structural Characterization of Lanthanide (III) Texaphyrin, " *Inorganic Chemistry*, 32(14):3175–3187, 1993.

Beilstein, "2–Äthlamino–2–methyl–propoanol–(1)", *Beilstein's Handbuch*, 4:785, 1950.

Fasman, "Tentative Rules for Carbohydrate Nomenclature Part 1 (1969), " *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexex and Their Applications to Magnetic Resonance Imaging and Photodynamic Therapy, " *Abstracts of Papers*, Part 1, 204th ACS National Meeting, Aug. 23–28, 1992, Washington, DC.

Sessler et al., "Synthesis and Applications of Schiff–Base Derived Expanded Porphyrins, "*Abstracts of Papers*, Part 1, 204th ACS National Meeting, Aug. 23–28, 1992, Washington, DC.

Sessler, Jonathan L., "Texas–Sized Molecule, " *Discovery*, 13(1):44–49, 1993.

Sessler et al., "Photodynamic Inactivation of Enveloped Viruses Using Sapphyrin, a 22π–Electron expanded Porphyrin: Possible Approaches to Prophylactic Blood Purification Protocols, " *SPIE Photodynamic Theraphy: Mechanism II.* 1203:233–245, 1990.

Maiya et al., "Ground–and Excited–State Spectral and Redox Properties of Cadmium(II) Texaphyrin, " *Journal of Physical Chemistry*, 93(24):8111–8115, 1989.

Sessler et al., "Texaphyrins: Synthesis and Applications, " *Accounts of Chemical Research*, 27(2):43–50, 1994.

Leff, "Texas 'Son–of–Porphyrin' Molecule Lassos Europium to Kill Drug Resistance Gene, " *BioWorld Today*, 5(156):1, 1994.

Young et al., "Preclinical Evaluation of Gadolinium (III) Texaphyrin Complex. A New Paramagnetic Contrast Agent for Magnetic Resonance Imaging, " *Investigative Radiology*, 29(3):330–338, 1994.

Dietrich et al., "Proton Coupled Membrane Transport of Anions Mediated by Cryptate Carriers, " *J. Chem. Soc. Chem. Comm.*, 1988, 11:691–692.

Dixon et al., "Molecular Recognition: Bis–Acylguanidiniums Provide a Simple Family of Receptors for Photodiesters, " *J. Am. Chem. Soc.*, 1992, 114:365–366.

Furuta et al., "Enhanced Transport of Nucleosides and Nucleoside Analogues with Complementary Base–Pairing Agents, " *Journal of the American Chemical Society*, 1991, 113:4706–4707.

Galán et al., "A Synthetic Receptor for Dinucleotides, " *J. Am. Chem. Soc.*, 1991, 113:9424–9425.

Galán et al., "Selective Complexation of Adenosine Monophosphate Nucleotides By Rigid Bicyclic Guanidinum Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing and Anion Binding Site, an Intercalcator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anions Receptors," *J. Org. Chem.*, 1990, 55(1):46–48.

Kimura, "Macrocyclic Polyamines as Biological Cation and Anion Complexones–An Application to Calculi Dissolution," 113–141.

Li and Diederich, "Carriers for Liquid Membrane Transport of Nucleotide 5'–Triphosphates," *J. Org. Chem.*, 192, 47:3449–3454.

Marks and Stojakowvic, "Large Metal Ion–Centered Template Reactions. Chemical and Spectral Studies of the 'Superphthalocyanine' Dioxocyclopentakis (1–iminoisoindolinato)uranium (VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases–Superiority of Macrobicycid Host Molecules," *Angew. Chem. Int. Ed. Engl.*, 1991, 30(4):442–444.

Sessler et al., "Anion Binding: A New Direction In Porphyrin–Related Research," *Pure & Applied Chem.*, 65(3):393–398, 1993.

Sessler et al., "Synthesis and Binding Properties of Monomeric and Dimeric Guanine and Cyctosine Amine Derivatives," *J. Org. Chem.*, 1992, 47:826–834.

Aoyama et al., "Multi–Point Interaction of Phosphates with Protonated Phyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Ragid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine for Guanosine Nucleotides Using a Cytosine–Pendant Triamine Host as the Sensory Element," *Analytical Chemistry*, 1992, 64(8):960–964.

Wang et al., "Pyrrole chemistry. XVII. Alkylation of the pyrrolyl ambident anion," *Can. J. Chem.*, 55:4112–4116, 1977.

Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler, et al., "Godolinium (III) Texaphyrin: A Novel MRI Contrast Agent," *Journal of the American Chemical Society*, 115(22):10,368–10, 369,1993.

Iverson et al., "Interactions Between Expanded Porphyrins and Nucleic Acids," *Pure Applied Chemistry*, 66(4): 845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng 1992, 1645 (Proc. Opt. Methods Tumor Treat. Dect: Mech. Tech. Photodyn. Ther.*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europeium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribuonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA.FE(II)," *Proc. Natl. Acad. Sci. USA*, 82:968–972, 1985.

Le Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Le Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:4464–471, 1986.

Groves and Farrell, "DNA Cleavage by a Metal Chelating Tricationic Porphyrin," *J. Am. Chem. Soc.,*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer bis(Di–Isobutyl Octadecysiloxy)Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen––Derivatized Oligonucleoside Methylphosphonates to Single–Stranded DNA," *Bioconjugate Chem.*, 1:82–88, 1990.

Boutourine et al., "Fullerene–Oligonucleotide Conjugates: Photo–Induced Sequence Specific DNA Cleaves", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4): 316–322, 1994.

Fedorova et al., "Palladium(II)–Coproporphyrin I as a Photoacivable Group in Sequence–Specific Modification of Nucleic Acids by Oligonucleotide Derivatives," *FEBS Lett.*, 259(2);335–337, 1990.

Morgan and Skalkos, "Second Generation Sensitizers: Where are We and Where Should We Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Resides of DNA," *Nucleic Acids Res.*, 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OPEc) and EtioPc)–Tetra–and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their Analos," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of Metal Ions, Including $Mg^{2°}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111;4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111;186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Saphhyrin Carrier," *J. Am. Chem. Soc.*, 113;6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am.Chem. Soc.*, 111:2521–2527, 1989.

Kim and Chin, "Dimethyl Phosphate Hydrolysis at Neutral pH," *J.Am. Chem. Soc.*, 114;9792–9795, 1992.

Komiyama et al. "Unprecedentedly Fast Hydrolysis of the RNA Dinucleoside Monophosphates ApA and UpU by Rare Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical–Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3′,5′-= Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Shelton and Morrow, "Catalytic Transesterification and Hydrolysis of RNA by Zinc(II) Complexes," *Inorg. Chem.*, 30:4295–4299, 1991.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolase et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic and Neutral Substrates," in Transition Metals in Supramolecular Chemistry, L. Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 1994.

International Search Report mailed Feb. 22, 1994.

International Search Report mailed Feb. 3, 1994.

Barton and Zard, "A New Synthesis of Pyrroles from Nitroalkenes," *J. Chem. Soc., Chem. Commun.*, pp. 1098–1100 (1985), published in Europe.

Collman et al., "Synthesis of 'Face to Face' Porphyrin Dimers Linked by 5, 15–Substituents: Potential Binuclear Multielectron Redox Catalysts," *JACS*, 103:516–533 (1981).

Franck et al., "Einfache Biomimetische Porphyrin–Synthesen," *Liebigs Ann. Chem.*, 263–274 (1980).

Franck et al., "Synthese von Geschütztem Nor–und Homoporphobilinogen," *Liebigs Ann. Chem.*, 253–262 (1980).

Grigg et al., "Studies in Furan Chemistry. Part IV[1] 2,2′-Bifurans," *J. Chem. Soc.*, 976–981 (1966).

Iverson et al., "Phosphate Recognition by Sapphyrin. A New Approach to DNA Binding," *J. Am. Chem. Soc.*, 115:11022–11023 (1993).

Iverson et al., "Molecular Recognition of Anionic Species by Silica Gel Bound Sapphyrin," *J. Am. Chem. Soc.*, 116:2663–2664 (1994).

Kambe and Yasuda, "The Potassium Fluoride–Catalyzed Reaction. V. Aldol Condensation of Nitroalkanes and Aliphatic Aledhydes," *Bull. Chem. Soc.*, 41(6):1444–1446 (1968).

Král et al., "A Covalently Linked Sapphyrin Dimer. A New Receptor for Dicarboxylate Anions," *J. Am. Chem. Soc.*, 117:2953–2954 (1995).

Kral et al., "Synthetic Saphhyrin–Cytosine Conjugates: Carriers for Selective Nucleotide Transport at Neutral pH," *J Am Chem Soc*, 114:8704–8705 (1992).

Kus et al., "First Representatives of Porphyrinylnucleosides," *Tetrahedron Letters*, 5133–5134 (1990).

Maiya et al., "In Vitro Photodynamic Activity of Diprotonated Sapphyrin: a 22–pi–electron Pentapyrrolic Porphyrin––like Macrocycle," *Chem. Absts.*,112:348–349, Abstract #194584t (1990), published in USA.

Sessler et al., "Enhanced Transport of Fluoride Anion Effected Using Protonated Sapphyrin as a Carrier," *J Chem Soc Chem Comm*, 1732–1735 (1991).

Sessler et al., "In vitro photodynamic activity of diprotonated sapphyrin: a 22–π–electron pentapyrrolic prophyrin––like macrocycle," *Chem Abstr*, 112:348–349, 112:194584t (1990).

Sessler et al., "Phosphate Anion Chelation and Base–pairing. Design of Receptors and Carriers for Nucleotides and Nucleotide Analogs," *Supramolec. Chem.*, 1:209–220, 1993.

Sessler et al., "Synthetic and Structural Studies of Sapphyrin, a 22–π–Electron Pentapyrrolic 'Expanded Porphyrin'," *J Am Chem Soc*, 112:2810–2813 (1990).

Shionoya et al., "Diprotonated Sappphyrin: A Fluoride Selective Halide Anion Receptor," *J Am Chem Soc*, 114:5714–5722 (1992).

Tindall, "Esters of Nitroalcohols," *Industrial and Engineering Chemistry*, 33(1):65–66 (1941).

Král & Sessler, "Molecular Recognition via Base–pairing and Phosphate Chelation. Ditopic and Tritopic Sapphyrin––based Receptors for the Recognition and Transport of Nucleotide Monophosphates," *Tetrahedron*, 51(2):539–554 (1995).

Schmidt,"Anomeric–oxygen activation for glycoside synthesis: the trichloroacetimidate method," *Advance in Carbohydrate Chemistry and Biochemistry*, 50:21–123 (1994).

Verlhac & Gaudemer, "Water–Soluble Porphyrins and metalloporphyrins as photosensitizers is aerated aqueous solutions. I. Detection and determination of quantum yield of formation of singlet oxygen," *Nouveau Journal De Chimie*, 8:401–406 (1984).

Wardle, "The Surface of Malignant and Virus Transformed Cells," *Cell Surface Science in Medicine and Pathology*, Elsevier Science Publishing Co., Inc., New York, 19:552–561 (1985).

Whitfield et al., "Differential reactivity of carbohydrate hytdroxyls in glycosylations. II. The likely role of intramolecular hydrogen bonding of glycosylation reactions. Galactosylation of nucleoside 5'–dydroxyls for the syntheses of novel potential anticancer agents," *Can. J. Chem.*, 72:2225–2238 (1994).

5,594,136

TEXAPHYRIN SOLID SUPPORTS AND DEVICES

The U.S. government has certain rights in the present invention pursuant to grant AI 28845 from the National Institutes of Health.

The present application is a continuation-in-part application of copending U.S. Ser. No. 08/236,218 filed Apr. 28, 1994. U.S. Ser. No. 08/236,218 is a continuation-in-part application of PCT/US93/09994 (WO94/09003), filed Oct. 18, 1993; which is a continuation-in-part application of U.S. Ser. No. 07/964,607, filed Oct. 21, 1992 now U.S. Pat. No. 5,457,195. U.S. Ser. No. 07/964,607 is a continuation-in-part application of U.S. Ser. No. 07/454,298 filed Dec. 21, 1989, since issued as U.S. Pat. No. 5,159,065. The entire contents of the patent and patent applications are incorporated by reference herein.

FIELD OF THE INVENTION

The present invention relates to the field of macrocyclic expanded porphyrins and, more particularly, concerns texaphyrins and texaphyrin derivatives that are conjugated to a polymer or solid matrix to form a polymer- or matrix-supported texaphyrin. Disclosed are polymer-supported texaphyrins including silica gel, polyacrylamide, and polystyrene; matrix-supported texaphyrins including resins, plastics and glass; texaphyrin-bearing apparati and devices, such as chromatographic supports; and methods of making and using these solid-supported texaphyrins, e.g., as in the separation or purification of metals, anions and other molecular species, and in catalyzing various chemical reactions, such as phosphate ester hydrolysis.

BACKGROUND OF THE INVENTION

Expanded porphyrins are large pyrrole-containing macrocyclic analogues of the porphyrins. A number of expanded porphyrin systems are now known. Those fully conjugated examples that contain more than four pyrrolic subunits include the smaragdyrins, sapphyrins, pentaphyrins, hexaphyrins, and superphthalocyanines.

A class of expanded porphyrins was developed based on the Schiff base condensation between a diformyltripyrrane and an aromatic 1,2-diamine[1]. This class of expanded porphyrins, known as the texaphyrins, describes an aromatic $22\pi$ benzannulene containing both 18- and 22-$\pi$-electron delocalization pathways[1]. The stabilization gained when the texaphyrin macrocycle becomes aromatic allows for considerable chemistry that is not possible in other pyrrole based macrocyclic systems.

The texaphyrins previously described, however, are known only to be of the character such that they are monomers and aggregated monomers in solution. Thus, even though the texaphyrins possess absolutely unique properties, their uses have previously been limited to homogeneous systems, not allowing for the facile separation of the texaphyrin following the procedure. This deficiency limited the utility of texaphyrins to potential applications where the texaphyrin compound could be removed readily following the procedure in which it was used.

The development of a texaphyrin that remains in contact with solution but is mechanically separated would, therefore, represent a significant advance. Such systems would have potential for use in improved applications in photodynamic therapy (PDT) and magnetic resonance imaging enhancement (MRI). They would also be of use in certain separation applications, including those based on high performance liquid chromatography (HPLC).

Immobilized texaphyrin systems would be especially useful if they could be made to retain the enhanced stability found when a texaphyrin is complexed to a lanthanide metal. Indeed, there is a significant need in the art for such a system as there is currently no means for effecting the stable complexation of lanthanides on a solid-support. The development of such a system would allow for heterogeneous catalysis, where it is important for the substrate to remain distinct from the metal complex.

The potential for subjecting solid-supported texaphyrins to harsh conditions, such as elevated temperatures and organic solvents, without breakdown of the catalyst would also be significantly increased. The development of immobilized texaphyrins could also prove to be useful in other areas, such as in the catalysis of certain hydrolytic reactions and the concomitant separation or purification of the individual products.

SUMMARY OF THE INVENTION

The present invention addresses the above and several other shortcomings in the prior art through the synthesis of various matrix-supported expanded porphyrin compositions and devices. In particular aspects, the invention provides novel matrix-supported texaphyrins, including texaphyrin-containing chromatographic supports and devices, including catheters. Methods of making such matrix-supported texaphyrins are also disclosed, as are methods of using these compositions and devices, for example, in the separation and purification of anions or neutral molecular species, in the hydrolysis of molecules containing phosphate esters, as catalysts for hydrogenation and polymerization reactions and in photodynamic therapy (PDT) and magnetic resonance imaging enhancement (MRI).

The synthesis of texaphyrin compounds linked to solid-support systems represents a considerable advantage, not only in terms of lanthanide complexation, but also as it allows binding of other metals and anions under conditions of site isolation. This, in turn, provides an important advantage in applications involving chromatography, such as the separation of molecular species or in the hydrolysis of compounds and separation of products, in a variety of catalytic mechanisms, including racemate resolution, and in MRI and PDT.

The matrix of the matrix-supported texaphyrin may be a polymeric- or a solid-support matrix. A polymer of a polymer-support matrix may be polystyrene, polyethylene, polyacrylamide, polypropylene, polyamide, Merrifield resin, sepharose, agarose, polystyrene, polydivinylbenzene, cellulose, alginic acid, chitosan, chitin, polystyrene-benzhydrylamine resin, an acrylic ester polymer, a lactic acid polymer, a texaphyrin multimer or a sapphyrin multimer. The solid-support may be silica, silica gel, amino-functionalized silica gel, alumina, clay, zeolite, glass, controlled pore glass or montmorillonite.

The invention therefore encompasses texaphyrin derivatives, conjugates and polymers thereof, as formulated into matrix-supported texaphyrins. In a general and overall sense, included within the novel compositions of the invention are matrix-supported texaphyrins that include one or more texaphyrin monomers, texaphyrin derivatives or conjugates or polymers thereof, whether or not the matrix-supported material also contains other groups, such as additional functional groups, or even sapphyrins.

As used herein, a texaphyrin is defined as a class of expanded porphyrins that is based on the Schiff base condensation between a diformytripyrrole and an o-phenylenediamine. The synthesis of texaphyrins depends on the simple, high yielding synthesis of tripyrroles. Following the synthesis of the tripyrrole is an acid-catalyzed condensation between a diformyltripyrrole and an o-phenylenediamine derivative. This results in the production of tripyrrole-containing Schiff base macrocycles referred to as reduced or sp³ texaphyrins. Subsequent 4-electron oxidation either in the presence or absence of a metal cation gives rise to the final aromatic, or sp², form of the texaphyrin.

Any texaphyrin, or derivative thereof, may be linked to a solid-support in accordance with the present invention. Structure I sets forth the general structure for a texaphyrin macrocycle.

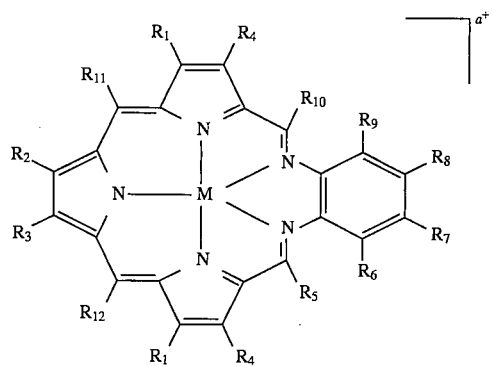

Texaphyrins may have a variety of substituents at the various R positions, as exemplified by hydrogen, halide, hydroxyl, alkyl, alkene, alkyne, aryl, haloalkyl, nitro, formyl, acyl, hydroxyalkyl, oxyalkyl, oxyhydroxyalkyl, glycol, polyglycol, thiol, thioalkyl, aminoalkyl, alkoxyalkyl, aryloxyalkyl, alkyloxycarbonyl, aryloxycarbonyl, aldehyde, ether, ketone, carboxylic acid, saccharide, phosphate, phosphonate, sulfate, phosphate substituted alkyl, phosphonate substituted alkyl, sulfate substituted alkyl, carboxy, carboxyalkyl, carboxyamidealkyl, a nucleobase, modified nucleobase, oligonucleotide, antibody, hormone, amino acid, peptide, polypeptide, a peptide having affinity for a biological receptor, a sugar, sugar derivative, polysaccharide, alkylating agent, steroid, steroid derivative, one or more sapphyrins, rubyrins, texaphyrins or derivatives thereof. However, it will be understood that the foregoing list is exemplary and is not meant to be exhaustive. M is hydrogen or a metal cation.

Structures II and III show texaphyrins bonded to a solid-support (SS). The texaphyrin R groups and M may be those described for structure I. In structures II and III, X represents the group of the texaphyrin for use in bonding and Y represents the group of the matrix solid-support (SS) for use in bonding; XY thus represents the linker between a texaphyrin and a matrix support.

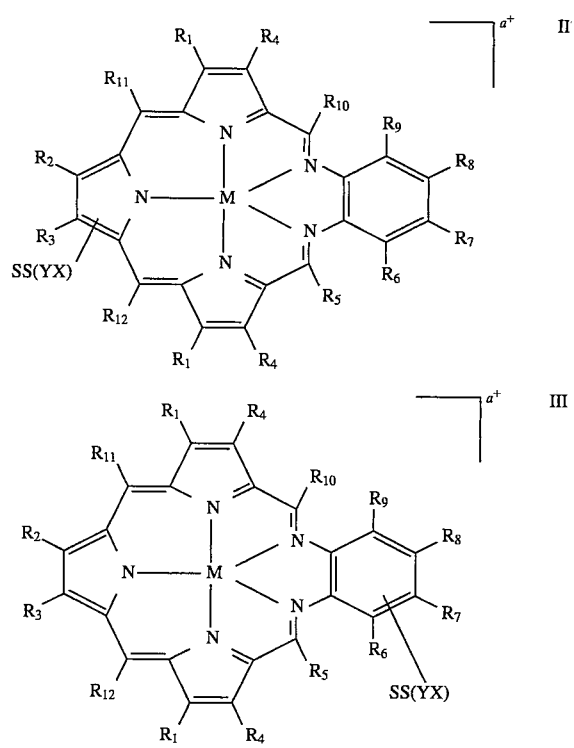

The matrix-supported texaphyrins of the present invention are useful for ester bond hydrolysis, heterogeneous catalysis, anion binding, separation of molecules such as nucleotides and oligonucleotides, magnetic resonance imaging, photodynamic therapy, or DNA photocleavage, for example.

An embodiment of the present invention is a method for separating a first molecule from a mixture of at least two molecules. The method comprises the step of contacting a matrix-supported texaphyrin metal complex with the mixture to separate the first molecule. A further embodiment is a method for hydrolysing a phosphate ester, the method comprising the step of contacting a matrix-supported texaphyrin metal complex where the metal cation has catalytic activity for ester bond hydrolysis in aqueous solution with the phosphate ester to cleave the ester. A method for conducting a chemical reaction catalyzed by a lanthanide metal cation is also an aspect of the present invention. This method comprises the step of contacting a matrix-supported texaphyrin lanthanide metal complex with a composition comprising the substrates for the chemical reaction. Matrix-supported texaphyrins are further useful as a medical device, such as a catheter, implant, interface or artificial joint.

Another embodiment of the present invention is a method of magnetic resonance imaging of a subject. The method comprises administering a matrix-supported texaphyrin paramagnetic metal complex to the subject; and imaging the subject by reference to the matrix-supported texaphyrin paramagnetic metal complex.

A method of light-induced singlet oxygen production is also as aspect of the present invention. This method comprises subjecting a matrix-supported texaphyrin to light in the presence of oxygen. The texaphyrin is a photosensitive texaphyrin, i.e., either unmetallated or complexed with a diamagnetic metal. In further applications of the photosensitivity of texaphyrins, the present invention also includes a method of photodynamic tumor therapy comprising, i) contacting a matrix-supported texaphyrin with a composition suspected of having tumor cells, and ii) photoirradiating the matrix-supported texaphyrin in contact with the composition; and a method for deactivating a retrovirus or an enveloped virus comprising, i) contacting a matrix-supported texaphyrin with a composition suspected of having a retrovirus or enveloped virus, and ii) photoirradiating the matrix-supported texaphyrin in contact with the composition.

A further aspect of the present invention involves the realization that novel expanded porphyrins, and particularly, texaphyrin structures may be prepared through the construction of polymers and oligomers, generically referred to as "multimers." As used herein, the terms "multimer" is intended to refer to any compound that includes at least two texaphyrin macrocycles joined covalently. The terms "oligomer" and "polymer" are generally understood to be overlapping in terms of defining a given length. However, it will still be appreciated that a texaphyrin "oligomer" or "oligotexaphyrin" refers to structures having about 2 or 3, and more preferably, about 10, 15, 20 or 30 texaphyrin units per molecule, up to and including about 40 or 50 units. On the other hand, "polymers" and "polytexaphyrin" are texaphyrincontaining structures that generally have upwards of about 40 or 50 texaphyrin units, up to an including about 80, 100 or 150 texaphyrin units, or even up to about 200 texaphyrin units or even more.

The texaphyrin oligomers and polymers of the invention also include texaphyrin dimers and trimers. The various texaphyrin oligomers and polymers encompassed by the present invention are represented by, for example, polymers in which n, the number of individual texaphyrin derivative units, may be about 5, 10, 20, 30 or 40, for texaphyrin oligomers, and about 50, 75, 100, 150 or about 200 or so for texaphyrin polymers.

In yet still further embodiments, the invention concerns compositions that are composed of a texaphyrin derivative in accordance with any one of the embodiments discussed above, particularly the polymer-supported texaphyrin, complexed to a second compound.

In still further embodiments, the invention concerns a method for forming a complex between a texaphyrin derivative and a second compound, wherein the method involves preparing a texaphyrin derivative as described above, including the polymer-supported forms such as silica-, Merrifield resin-, glass-, plastic- and organic polymer-supported texaphyrins; obtaining the second compound; and contacting the texaphyrin derivative with the second compound under conditions effective to allow the formation of a complex between the texaphyrin derivative and the second compound.

DETAILED DESCRIPTION OF THE PREFERRED EMBODIMENTS

Structure I provides a texaphyrin having substituent groups, $R_1$–$R_{12}$. A variety of texaphyrin derivatives and their metal complexes have been prepared, for example, as described in U.S. Pat. Nos. 4,935,498, 5,162,509, 5,252,720, 5,292,414, 5,272,142, 5,256,399 and 5,369,101; PCT publications WO 94/09003 and WO/94,29316 and application Ser. Nos. 07/964,607, 08/015,208, 08/098,514, 08/100,093, 08/112,871, 08/112,786, 08/112,872, 08/135,118, 08/196, 964, 08/207,845, 08/227,370 and 08/310,501, each of which is incorporated herein by reference. A texaphyrin in accordance with any of the above-named references may be linked to a solid-support in accordance with the present invention.

With reference to structure I, M may be hydrogen, a divalent metal cation or a trivalent metal cation; and $R_1$–$R_4$, $R_7$ and $R_8$ may be separately and independently hydrogen, halide, hydroxyl, alkyl, alkene, alkyne, aryl, haloalkyl, nitro, formyl, acyl, hydroxyalkyl, oxyalkyl, oxyhydroxyalkyl, glycol, polyglycol, thiol, thioalkyl, aminoalkyl, alkoxyalkyl, aryloxyalkyl, alkyloxycarbonyl, aryloxycarbonyl, aldehyde, ether, ketone, carboxylic acid, saccharide, phosphate, phosphonate, sulfate, phosphate substituted alkyl, phosphonate substituted alkyl, sulfate substituted alkyl, carboxy, carboxyalkyl, carboxyamidealkyl, a nucleobase, modified nucleobase, oligonucleotide, antibody, hormone, amino acid, peptide, polypeptide, a peptide having affinity for a biological receptor, a sugar, sugar derivative, polysaccharide, alkylating agent, steroid, steroid derivative, one or more sapphyrins, rubyrins, texaphyrins or derivatives thereof; or a couple that is coupled to an oligonucleotide, an antibody, a hormone, a peptide having affinity for a biological receptor or a sapphyrin molecule; $R_6$ and $R_9$ may be independently selected from the groups of $R_1$–$R_4$, $R_7$ and $R_8$, with the proviso that the halide is other than iodide and the haloalkyl is other than iodoalkyl; and $R_5$ and $R_{10}$–$R_{12}$ may be independently hydrogen, alkyl, aryl, hydroxyalkyl, oxyalkyl, oxyhydroxyalkyl, carboxyalkyl, carboxyamidealkyl or a couple that is coupled to a saccharide, an oligonucleotide, an antibody, a hormone, a peptide having affinity for a biological receptor, or a sapphyrin molecule.

M may be a divalent metallic cation, such as Ca(II), Mn(II), Co(II), Ni(II), Zn(II), Cd(II), Hg(II), Sm(II), Fe(II), Cu(II), or $UO_2$(II), with "a" being 1; or M may be a trivalent metal cation, such as Mn(III), Co(III), Ni(III), Fe(III), Ho(III), Ce(III), Y(III), In(III), Pr(III), Nd(III), Sm(III), Sc(III), Eu(III), Gd(III), Tb(III), Dy(III), Er(III), Tm(III), Yb(III), Lu(III), La(III), or U(III); in which case, "a" would be 2. Representative paramagnetic metal cations are Sm(III), Eu(III), Gd(III), and Dy(III). Representative diamagnetic metal cations are La(III), Lu(III), and Y(III). As would be apparent to one skilled in the art, the charge "a" would be adjusted so as to account for the choice of metal, M, the pH under consideration, and the substituents $R_1$–$R_{12}$. For instance, if $R_1$=carboxyl and $R_2$–$R_{12}$=alkyl and the metal, M=Gd(III), and the solution is pH=7 (so that $R_1$=$CO_2-$), the charge "a" would be zero. The charge would be negative when substituents have a sufficient number of negative charges, for example, when a substituent is an oligonucleotide. The charge would be +5, for example, when the M is Gd(III) and the net charge of a substituent(s) is three positive charges.

In the texaphyrins represented by structure I, $R_1$, $R_2$, $R_3$, $R_4$ and $R_5$ may be attached via a carbon-carbon or a carbon-oxygen bond. Also, where oxyhydroxyalkyl groups are present, they may be further substituted, bearing a substituent in lieu of hydrogen of the hydroxyl substituent. Additionally, where carboxyamidealkyl groups are present, they may have a secondary or tertiary amide linkage.

The aryl group may be phenyl, or a phenyl having a nitro, carboxy, sulfonic acid, hydroxy, oxyalkyl or a halide substituent. Oxyhydroxyalkyls may be alkyls having independently hydroxy substituents and ether branches. Carboxyalkyl groups may be alkyls having a carboxyl substituted ether, an amide substituted ether or a tertiary amide removed from an ether. Couples may be amide, thiol, thioether or ether covalent bonds.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by two or more functional groups as described herein.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane, straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–3. A preferred oxyalkyl is $O(CH_2CH_2O)_x CH_3$ where x=1–100, preferably 1–10, and more preferably, 2–3.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate substituted alkyls include alkyls as described above substituted by one or more sulfate groups, a representative example of which is diethyl sulfate (($C_2H_5$)$_2SO_4$); they also include simple anionic sulfate or sulfonate substituents such as —$C_2H_5SO_3$—.

Representative examples of phosphates include phosphate or polyphosphate groups. Representative examples of phosphate substituted alkyls include alkyls as described above substituted by one or more phosphate or polyphosphate groups. Representative examples of phosphonate substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R'' is a functional group as described herein.

Representative examples of useful amines include a primary, secondary or tertiary amine of an alkyl as described hereinabove.

Representative examples of useful oligonucleotides include nucleotides, oligonucleotides and polynucleotides primarily composed of adenine, cytosine, guanine, thymine or uracil bases. It is understood that the term nucleotide as used herein refers to both naturally-occurring and synthetic nucleotides, poly- and oligonucleotides and to analogs and derivatives thereof such as methylphosphonates, phosphotriesters, phosphorothioates and phosphoramidates.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$.

The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to $2n+1$, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl, or $C_mH_{((2m+1)-r)}O_zR^b_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl, or $C_mH_{((2m+1)-r)}O_zR^b_r$, where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than ((2n+1)–q), q is zero or a positive integer less than or equal to 2n+1, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)–2w), R is H, alkyl, hydroxyalkyl or $C_mH_{((2m+1)-r)}O_zR^b_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

In structures II and III, X may be [—$(CH_2)_n$—]—$NH_2$ where n is an integer from 0 to 20, OH, $CO_2H$, Cl, Br, I, OH, NCO, NCS, NC, C≡CH, CH=$CH_2$, MgCl, ZnCl, Li, a nucleotide or an oligonucleotide. These groups may be at any of the substituents, $R_1$–$R_4$, $R_7$ or $R_8$, of the texaphyrin. The X group reacts with available groups, termed Y, present on, or previously inserted into, the polymeric or solid-support matrix. Y in structures II and III may thus be [—$(CH_2)_n$—]—OH where n is an integer from 0 to 20, $NH_2$, $CO_2H$, Cl, Br, I, NCO, NCS, oxirane, C≡CH, MgCl, ZnCl, Li, a nucleotide or an oligonucleotide. Conversely, X may have the hydroxyl group and Y may have the amino group. The combination of reactive groups, X and Y, may give rise to a polymer-supported texaphyrin in which the texaphyrin is joined to the polymeric or solid-support matrix via an ether, ester, amide, amine, carbamate, urea, —CH=CH—, —C≡C—, —$(CH_2)_m$— where m is an integer from 1 to 20, functionalized alkyl or aryl bond or via an oligonucleotide or even a peptide.

In all cases, the solid-support may be silica, silica gel, amino-functionalized silica gel, alumina, clay, zeolite, glass, controlled pore glass, montmorillonite, polystyrene, polyethylene, polyacrylamide, polypropylene, polyamide, Merrifield resin, sepharose, agarose, polystyrene, polydivinylbenzene, cellulose, alginic acid, chitosan, chitin, polystyrene-benzhydrylamine resin, an acrylic ester polymer, a lactic acid polymer, polyurethane, polyvinylchloride, nylon, latex, silicone rubber, a halogenated polyethylene, an organosilicone, a biocompatible ceramic, bioglass or sintered hydroxyapatite. A preferred solid support is silica gel.

Structures IV and V show examples of structures II and III, respectively, representing solid-supported texaphyrins linked to silica gel. In these examples, X=$O(CH_2)_n$ where n=1–6, and SS represents 3-aminopropyl silica gel.

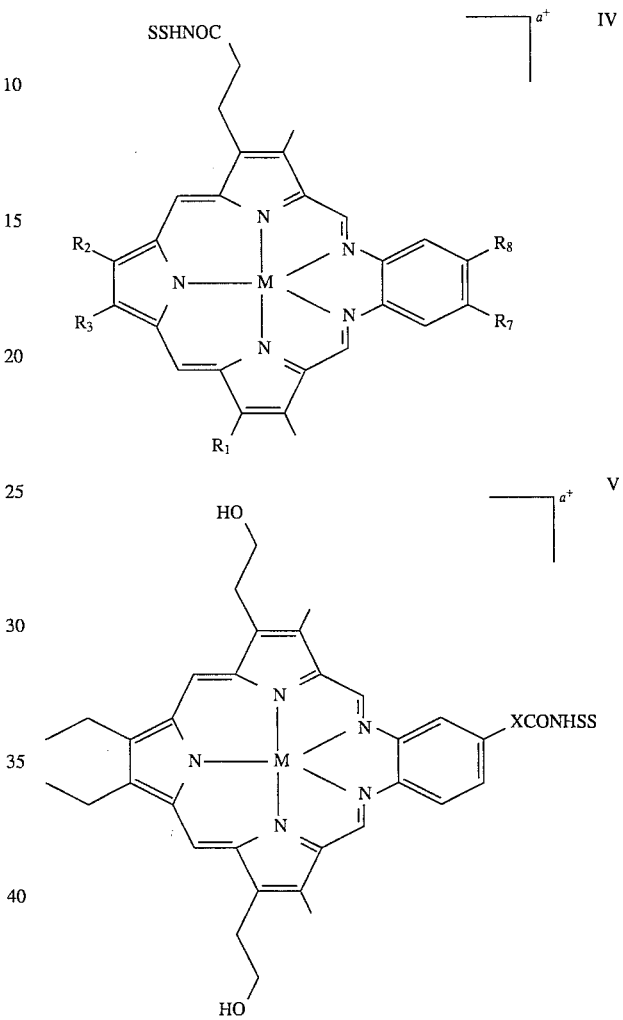

Suitable methods for use in synthesizing a variety of texaphyrins with different R groups will be known to those of skill in the art, in light of disclosures such as, e.g., U.S. Pat. Nos. 4,935,498 and 5,252,720 and PCT/US 95/01996. Each of the foregoing documents are incorporated herein by reference for the purpose of supplementing the present teaching as to the synthesis of texaphyrin and texaphyrin derivatives.

The texaphyrin units for use in conjugating to a solid-support may also be dimers, trimers, oligomers or polymers of texaphyrins or texaphyrin derivatives alone; or may be dimers, trimers, oligomers or polymers of texaphyrins or texaphyrin derivatives in combination with other expanded porphyrins, such as sapphyrins or rubyrins. The texaphyrins may also be conjugated to other units, such as alkyl chains or nucleobases, prior to linking to a polymer or solid-support.

The term a "texaphyrin-metal complex", as used herein, refers to an aromatic pentadentate expanded porphyrin analog metal complex, that may have various appended functional groups. A wide range of metals may be complexed with a texaphyrin. These include, for example, divalent or trivalent metal cations of the lanthanide group or Lewis acidic cations. Examples of these include all of the lanthanide group with the exception of Pm(III), as represented by La(III), Nd(III), Sm(III), Sm(II), Gd(III), Tm(III), Lu(III), Eu(III) and Dy(III); and also Y(III), In(III), Ce(III) and Sc(III). Further divalent and trivalent metallic cations that may be bound to a matrix-supported texaphyrin of the invention include Ca(II), Mn(II), Co(II), Ni(II), Zn(II), Cd(II), Hg(II), and Mn(III), Co(III), Ni(III), Fe(III), Cu(III), Ho(III), Pr(III), Tb(III), Er(III), Yb(III), with even V(III), Cr(II), and Cr(III) being possibilities for binding to texaphyrins.

The choice of metal ion for complexing to a texaphyrin will generally be dependent upon the use or uses intended for the matrix-supported texaphyrin. For example, metal ions that have catalytic activity for ester bond hydrolysis, such as Eu(III) or Dy(III), would be used to create a matrix-supported metallotexaphyrin for use in RNA hydrolytic cleavage.

Metal ions that have catalytic activity for hydrogenation and polymerization reactions, such as Sm(II), may be used to construct a matrix-supported metallotexaphyrin for use in heterogeneous catalysis. Also, by varying the metals, e.g., by changing from Gd(III) to Lu(III) or Ce(III), the texaphyrin compounds can be modified so as to have enhanced selectivity for various different anions such as phosphates and carboxylates.

Paramagnetic species, such as Gd(III), Cu(III), Sm(III), Eu(III), Dy(III), Ni(III), Co(II), Co(III), Fe(II) and Fe(III), and most preferably, Gd(III), that have utility in magnetic resonance imaging protocols are also useful metals for complexing with matrix-supported texaphyrins.

The use of diamagnetic species, such as La(III), Y(III) or Lu(III), is also encompassed within the present invention; such matrix-supported texaphyrins would then be useful in photodynamic therapy. Lu(II) or La(III) derivatives would thus be preferred in applications, such as in vitro purging of virus and cancer cells from blood or other bodily fluids, where the photodynamic production of singlet oxygen is of predicative importance. Also, $^{90}Y^{3+}$ and $^{111}In^{3+}$ derivatives would be of preference in radiotherapeutic and diagnostic applications.

However, in certain embodiments, the use of a texaphyrin that is not complexed to a metal ion is also contemplated. Such systems would be useful for the chromatography, capture and/or removal of metals, both on an analytical scale and an industrial one. These matrix-supported texaphyrins without central metal ions would thus provide an advantage in waste removal from, for instance, marine and agricultural environments.

In synthesizing a matrix-supported texaphyrin, the texaphyrin may be conjugated to the matrix at virtually any R position and using a wide range of R groups. For example, with reference to Structures II and III, the X group of the texaphyrin may be [—$(CH_2)_n$—]—$NH_2$ where n is an integer from 0 to 20, OH, $CO_2H$, Cl, Br, I, OH, NCO, NCS, NC, C≡CH, CH=$CH_2$, MgCl, ZnCl, Li, a nucleotide or an oligonucleotide. These groups would be reacted with available groups, termed Y, present on, or previously inserted into, the polymeric or solid-support matrix (termed SS in structures II and III). Y in structures II and III may thus be [—$(CH_2)_n$—]—OH, $NH_2$, $CO_2H$, Cl, Br, I, NCO, NCS, oxirane, C≡CH, MgCl, ZnCl, Li, a nucleotide or an oligonucleotide. The combination of reactive groups, X and Y, gives rise to a matrix-supported texaphyrin in which the texaphyrin is joined to the polymeric or solid-support matrix via an ether, ester, amide, amine, carbamate, urea, —CH=CH—, —C≡C—, —$(CH_2)_m$— where m is an integer from 1 to 20, functionalized alkyl or aryl bond or via an oligonucleotide or even a peptide.

Therefore, in selecting a polymeric or solid-support matrix, one would generally select one that comprises, or may be derivatized to comprise, a group that permits the formation of a covalent bond with a texaphyrin substituent. Groups such as aryl, silyl, siloxy, aminoaryl, amino, amidoaryl and silyloxy are examples of these.

The linker between a texaphyrin and a matrix may also be described using the formula: T—$(CH_2)_n$—A—$(CH_2)_m$—B, wherein T is any texaphyrin macrocycle or derivative or conjugate thereof; B is the polymeric matrix or solid-support matrix; and n and m are zero or integers of less than or equal to 20, or more preferably, of less than or equal to 10. Using this analysis, A may be alkyl, aryl, oxy, sulfide, amide, carbonyl, alkenyl, alkynyl, halide, alkylhalide, arylhalide, arenyl, hydroxyalkyl, glycol, polyglycol, thiol, alkylthiol, substituted alkyl, phosphate, phosphonate, sulfate, phosphate substituted alkyl or aryl, phosphonate substituted alkyl or aryl, sulfate substituted alkyl or aryl, carboxy, carboxyamide, ester, thiol-substituted carboxyamide, or derivatized carboxyamide.

The functionalization of a polymeric matrix or solid-support matrix may take any one of many forms, so long as the result is to derivatize the polymer or support so that a texaphyrin moiety may be attached or bonded to the support. In preferred embodiments, the polymeric or solid-support matrix will thus comprise, or will be derivatized to comprise, an aryl, silyl, siloxy, aminoaryl, amino, amidoaryl or silyloxy group, which group will form as a linking unit (linker) between the solid-support and the texaphyrin. Examples of linkages between the texaphyrin and the polymeric or solid-support matrix include: —$(CH_2)_3$—$(CH_2)_2$—$Si(R)_2$—O—; —$(CH_2)_3$—$Si(R)_2O$—; and —$(CH_2)_2$—Si—$(CH_2)_2O$—, where R may be siloxy, alkyl, hydroxyl, alkoxy, or oxygen, for example.

A variety of polymeric or solid-support matrices may be linked to a texaphyrin as disclosed herein. Although there is overlap in terminology, the polymers or matrices may be considered as inorganic polymers or matrices, organic polymers, copolymers and biocompatible polymers, all of which can be functionalized by those skilled in the art of chemical synthesis.

Examples of inorganic polymers or matrices include, for example, silica, silica gel, amino-functionalized silica gel, alumina, clay, zeolite, glass, controlled pore glass and montmorillonite, along with certain biocompatible materials. Certain examples of organic polymers include polystyrene, polyethylene, polyacrylamide, polypropylene, polyamides, Merrifield resin, sepharose, agarose; with copolymers being represented by polystyrene and polydivinylbenzene.

Polysaccharides are another group of organic polymers. These include cellulose and alginic acid and amino-polysaccharides, such as chitosan and chitin. In addition to amino-functionalized natural polymers, man-made amino-functionalized organic polymers are also contemplated, such as polystyrene-benzhydrylamine resin.

In addition to certain natural organic polymers, other biocompatible polymers include, for example, polyurethane, polyvinylchloride, nylon, latex, silicone rubber, halogenated polyethylenes, such as polytetrafluoroethylene (PTFE) and other Teflon® materials, organosilicones, e.g., Silastic® materials, and even biocompatible ceramics.

In terms of matrices for use in medical compositions and devices, these should be "biocompatible". This means that the matrix has all the features commonly associated with medical uses, in that it is in a form that does not produce an adverse, allergic or other untoward reaction when administered to an animal or human subject.

The choice of matrix material will differ according to the particular circumstances and the site of the body into which the device is to be inserted. Physical and chemical characteristics, such as, e.g., biocompatibility, biodegradability, strength, rigidity, interface properties and even cosmetic appearance may be considered in choosing a matrix, as is well known to those of skill in the art.

Non-biodegradable matrices will most often be employed in accordance with the polymer-supported texaphyrins, such as, sintered hydroxyapatite, bioglass, aluminates, or other bioceramic materials. Ceramic delivery systems are described in U.S. Pat. No. 4,596,574, incorporated herein by reference. Polymeric matrices that may also be employed include acrylic ester polymers and lactic acid polymers, as disclosed in U.S. Pat. Nos. 4,526,909, and 4,563,489, respectively, each incorporated herein by reference.

Naturally, the polymeric or solid-support matrix that forms the supporting part of the matrix-supported texaphyrin will be chosen according to the intended function and use of the resultant composition. For example, silica gel may be used to prepare bonded, texaphyrin-substituted silica gels for formulation into columns for use in medium to high pressure applications, such as in analytical and preparative HPLC separation technology. Alternatively, for low pressure applications, organic polymer-based texaphyrins may be prepared, such as texaphyrin-substituted Merrifield resins. Also, a glass support such as a glass capillary tube, may be employed to prepare a glass-supported texaphyrin for use, e.g., in analytical capillary electrophoresis (CE).

Further compositions of the invention include medical devices that comprise a texaphyrin linked to a surface of the device, for example, a catheter in which one or more texaphyrins are linked to a surface of the catheter; an orthopedic implant or interface or an artificial joint. Such implants themselves and functional parts of implants, such as, e.g., surgical screws, pins, and the like are encompassed. In preferred embodiments, it is contemplated that the surface or surfaces of a catheter, implant, or a portion thereof, such as a screw, will be coated with a metallotexaphyrin complexed to a paramagnetic metal ion, such as Cu(III), Ni(III), Co(II), Co(III), Fe(II) or Fe(III), and most preferably, Gd(III), prior to implantation.

The range of matrix-supported texaphyrins contemplated by the present inventors, and described herein, extends to second and third generation compositions designed to separate molecular and ionic species based upon further specific binding modes, in addition to the basic neutral entity or phosphate recognition provided by the metallotexaphyrin moiety. One particular example concerns matrix-supported texaphyrins that further comprise long chain alkyl groups, such as, those of the formula $CH_3-(CH_2)_n$, where n=1–20, such as, e.g., $CH_3(CH_2)_7$, $CH_3(CH_2)_{11}$ or $CH_3(CH_2)_{17}$, and also groups such as $C_6H_5CONH$, phenyl, naphthyl, substituted naphthyl, and the like, to impart hydrophobic and $\pi$—$\pi$ interaction separation capacity to the modified solid-support. A second example contemplated concerns the use of matrix-supported texaphyrin constructs that also comprise nucleobase structures and thus allow separation of nucleobase-containing compounds on the basis of specific base-pairing interactions.

It is contemplated that further modified matrix-supported texaphyrins may be constructed by modifying either the appended texaphyrin moiety or the polymeric or solid-support matrix itself. For example, in the case of texaphyrin-nucleobase columns, a texaphyrin-nucleobase conjugate may be used in the initial synthesis, or alternatively, the nucleobase units may be later appended onto available groups of the texaphyrin or onto available groups of the solid-support itself. Where the addition of long chain alkyl groups is desired, it is contemplated that such groups will generally be introduced onto the surface of the polymeric or solid-support matrix, although the invention is not limited solely to this mode of addition.

The range of matrix-supported texaphyrin-nucleobase constructs contemplated includes a wide variety of nucleobase compounds. The choice of compound will be tailored to suit the intended function of the solid-support, such as, to bind to a specific nucleobase-containing compound which one desires to purify, remove, or otherwise separate from a mixture of compounds. The nucleobase-containing group, whether bonded to the texaphyrin or to the support matrix, may therefore comprise any purine or pyrimidine base including adenine, cytosine, guanine, thymidine, uridine and inosine, or any analog or derivative thereof, including antimetabolite nucleobases, nucleobase derivatives shown in Table 2, and even protected nucleobases.

The texaphyrin-nucleobase solid-support matrices may also have appended nucleosides, nucleotides and oligonucleotides, for example, oligonucleotides comprising between two and about 10 nucleobase units. Constructs bearing a selected nucleotide or oligonucleotide may be formulated into columns, filters or other solid materials such as capillary tubes, and used to selectively bind compounds which include the complementary nucleotide or oligo or polynucleotides containing substantially complementary sequences. As used herein, a substantially complementary sequence is one which the nucleotides generally base pair with the complementary nucleotide and in which there are very few base pair mismatches.

Matrix-supported texaphyrins of the second and third generation may also comprise functional groups designed to alter the chemical capabilities of the metallotexaphyrins. For example, the texaphyrin may include an imidazole ring or an arginine residue. The texaphyrin may also have an attached chiral group, for example: a D-sugar unit, such as D-glucopyranosyl; an L-sugar unit; an L-amino acid, such as L-alanine or L-phenylalanine; an oligopeptide; an oligosaccharide; or a chiral binaphthyl system.

Although described in terms of texaphyrins, the present invention also encompasses other matrix-supported expanded porphyrins, including sapphyrins and rubyrins, that have been joined to a polymeric or solid-support matrix. The use of an expanded porphyrin capable of binding anions, and preferably, those capable of phosphate or nitrate chelation, is particularly contemplated. In such embodiments, the use of expanded porphyrins of the rubyrin class, and particularly of the sapphyrin class, is envisioned.

The synthesis of rubyrin and derivatives thereof is described in detail in U.S. patent application Ser. No. 08/015,208, incorporated herein by reference. Polymer-supported rubyrins may be prepared using a rubyrin compound as the starting material in combination with the synthetic methodology disclosed in the present application. In other embodiments, the invention also provides for the generation of polymer-supported sapphyrins comprising a sapphyrin unit, derivative, conjugate or polymer thereof linked to a support. In addition to the present application, the generation of polymer-supported sapphyrins is described in PCT publication WO 94/09003, incorporated herein by reference.

The present invention also provides methods for using the matrix-supported texaphyrins and expanded porphyrins described above in separating a first molecule from a mixture of at least two molecules. In the present sense, the term "molecule" is being used for simplicity to refer to both molecular and atomic structures and thus encompasses species such as metal cations like those of the trivalent lanthanide series and atomic anions such as $Cl^-$, $Br^-$, and $I^-$. The columns, capillary tubes, filters, devices and the like, of the invention are contemplated to be of most use in separating neutral or negatively-charged entities that would be bound as ligands to the texaphyrin metal centers. Such species could be neutral materials containing, e.g., hydroxyls; or anionic materials, such as those bearing a phosphate, phosphonate, phosphate ester, arsenate, arsenate ester, carboxylate, nitrate, sulfate, sulfonate or sugar moiety within their structure.

However, it is envisioned that the matrix-supported texaphyrin constructs will generally be of most use for separating oligonucleotides such as RNA and DNA that contain phosphate esters. Here, in addition to the separation embodiment, it is contemplated that these same solid-supports could be used to effect catalytic hydrolysis of the phosphate ester bonds, as described in the present detailed examples.

To separate a first molecule, such as an RNA fragment of a given length from a mixture containing at least one other oligonucleotide of similar but not identical composition in accordance with the invention, one would generally contact a matrix support bearing a texaphyrin with the mixture, thereby separating the first molecule. The contacting may, generally, take the form of passing a solution containing the mixture to be separated, or purified, over a column to which texaphyrins are appended.

The separation process generally entails binding the mixture containing the molecules or species to be separated to a matrix-supported texaphyrin, such as a column, capillary tube, filter, filter cartridge or such like, and then, subsequently, removing, or eluting, the bound species in such a way as to result in the formation of distinct fractions containing molecules which have been separated from each other.

The phrases "separated" and "purified" in this context are intended to mean separated away from, and purified relative to, the degree of purity of an individual molecule, atom or species in the original composition. Although it is contemplated that the methods of the invention may be employed to achieve high resolution separation of, e.g., oligonucleotides, there is no requirement that such high degrees of purity always be achieved. Separation methods that result in less substantially separated species also have utility and are thus encompassed by the claimed invention.

The methods for separating or purifying anionic, cationic, or even neutral species by contacting solutions of various mixtures with a functionalized solid-support are generally encompassed by the terms "chromatographic or electrophoretic separation methods". The chromatographic methods are those using columns, such as HPLC columns, whereas the electrophoretic separation methods are exemplified by those using capillary tubes. Various chromatographic and electrophoretic separation techniques are well known in the art, and any such method may be employed in connection with the invention simply by preparing a polymer-supported texaphyrin and packaging or formulating it to give a device to be used as the central component of the separation technique.

In separating anionic, cationic or even neutral species, from a mixture in accordance with the invention, it is contemplated that one would generally first formulate the mixture to be separated into a solution. One would then contact the matrix-supported texaphyrin with the solution under conditions effective, and for a time period sufficient, to allow binding of the anionic, cationic or neutral species to the solid-support. This is straightforward and may be achieved simply by passing the solution over the solid material with or without the use of pressure or an electrostatic field. The anionic or neutral species will, in the simplest case, bind specifically to the metal center of the texaphyrin moiety. Where the matrix-supported texaphyrins bear other groups, such as long chain alkyl groups, nucleobases, or aromatic residues, other portions of the contemplated substrates, such as hydrophobic portions or purine and pyrimidine nucleobase substituents in this case, e.g., of oligonucleotides will also likely specifically bind to these additional functional groups or interact with the texaphyrin ring.

Suitable conditions effective to allow binding of the species to the solid-support will be chosen based upon considerations such as the number and type of the particular species to be separated, the purity of the resultant compositions desired, the particular type of texaphyrin and its complexed metal ion, other functional groups appended to the texaphyrin or to the solid-support matrix, and the like. After the initial binding stage, the solid-support may be washed with the same or other buffers of chosen stringency and for varying periods of time to remove any non-specifically bound species from the solid-support.

The matrix-supported texaphyrin with the bound species would next generally be treated to remove the bound species that may then be collected in a more separate and purified form than when applied, for example, collected in distinct fractions. This process will generally be achieved by washing the solid-support with a second solution effective to detach the bound anionic or neutral species, i.e., a solution effective to disrupt the specific binding between the species and the texaphyrin, metal center or between it and other functional groups incorporated within the texaphyrin structure or the support. Such separations, in the case of chromatographic applications would be useful both for analysis and purification procedures. In the case of capillary electrophoresis, however, they would be likely to be useful only for analysis.

The second solution will be distinct from that first used and, again, will be chosen based upon the particular application. It may, for example, have a different ionic strength, hydrophobicity or pH compared to the first solution and may contain different concentrations of salt or other chaotropic agents as desired. This removal process may be termed "elution" and the eluted material will generally be collected in relatively small fractions, such as in 1 to 2 ml fractions, and preferably in fractions of about 1 ml or smaller, so that the fractions contain one or more detached species that have been separated or purified away from the total number of species in the starting composition. Alternatively, for analysis applications, the fractions could be much smaller, i.e. $\geq 10$ µl, and used only as a means of assessing by, e.g., optical absorbance, refractive index, or mass spectral fragmentation, the composition of a given fraction. From such an analysis one would then, in the usual way of the art, obtain a profile of the purity and composition of the original solution.

Any of the matrix-supported texaphyrin derivatives described above may be used as a separating apparatus in this regard, as may supports comprising a sapphyrin or rubyrin derivative, and those including nucleobase conjugates, long chain alkyl groups and oligonucleotides. Although a detailed understanding of the binding mechanisms is not necessary in practicing the present invention, it should be noted that the use of a texaphyrin generally relies on substrate binding to a metal center, whereas sapphyrin and rubyrin are based upon more direct anion chelation.

Regardless of the particular expanded porphyrin, the separating apparatus may use, for example, silica gel, Merrifield resins, glass, agarose or sepharose, polyacrylamide or another type of plastic as the support matrices and may be prepared in virtually any solid form including columns, filters, cartridges, tubes and thin layers. Their use in analytical and preparative modes in both research and clinical laboratories is envisioned, as is their use in medical and veterinary procedures, including various diagnostic embodiments.

It is contemplated that these novel matrix-supported expanded porphyrins will be found to be particularly useful in separating compounds which have nitrate or phosphate groups or phosphate esters within their structure. This includes separating or purifying purine- and pyrimidine-containing compounds, including nucleotides, oligonucleotides, gene fragments, nucleobase analogs, and derivatives such as antimetabolite purines and pyrimidines, e.g., AZT phosphate, dideoxycytidine phosphate, and other prodrugs used in the treatment of viral infections including HIV. The use of the methods and compositions of the invention in clinical analyses to distinguish active phosphorylated nucleotide analogs from naturally occurring phosphorylated products, such as AMP or GMP, is a further particular utility envisioned by the inventors.

Organophosphorus compounds, nitrate esters, as well as simple inorganic nitrate, nitrite, phosphate and phosphonate anions, particularly pesticides, herbicides, fungicides, marine pollutants and even chemical warfare agents may also be separated in the manner of the invention. For example, using polymer-supported expanded porphyrin constructs is envisioned to be of use in removing various such undesirable compounds from contaminated solutions, e.g., in waste-removal and treatment regimens.

As disclosed herein, nucleotide mono-, di- and tri-phosphates may be advantageously separated from each other using polymer-supported texaphyrins, as may mono-nucleotides, di-nucleotides and various length oligonucleotides, such as oligonucleotide probes and primers. The separation of larger polynucleotides, up to and including gene fragments, genes, and antisense constructs is also encompassed by the present invention. The sequence-specific purification of nucleotide-containing constructs is also envisioned, whereby specific oligonucleotides or polynucleotides, whether DNA or RNA species, may be obtained by employing second or third generation matrix-supported expanded porphyrins bearing appended oligonucleotides with specific sequences. This allows the separation of nucleotides and oligonucleotides not only on the basis of charge and length but also on the basis of nucleic acid type.

The present invention also provides methods for hydrolysing a phosphate ester bond. These methods generally comprise contacting a matrix-supported metal-texaphyrin (metallotexaphyrin) complex with a composition comprising one or more molecules or species that include within their structure a phosphate ester bond, in order to cleave said phosphate ester. This process generally takes the form of contacting the matrix-supported texaphyrin with a solution that includes the molecule(s) to be cleaved under conditions effective, and for a time period sufficient, to allow functional contact between the metal-complexed texaphyrin and the molecule. The functional interaction thus results in cleavage of the ester linkage.

The use of matrix-supported texaphyrins allows facile recovery of the catalyst without the risk of substrate or product contamination by the catalyst. Flow reactions are also possible using these "heterogeneous systems". These are therefore generally preferred over the batch processes possible with "homogeneous systems".

In such ester cleavage embodiments, the matrix-supported texaphyrin will be complexed to a metal ion, such as a divalent or trivalent metal cation, that has catalytic activity for ester bond hydrolysis, particularly in aqueous environments. Examples of useful metals that may be complexed with a texaphyrin in this manner are La(III), Nd(III), Sm(III), Gd(III), Tm(III), Lu(III), Eu(III), Dy(III), Y(III) and In(III); with Eu(III)- and Dy(III)-complexed texaphyrins being preferred in certain embodiments as these texaphyrin-metal complexes are particularly effective in mediating RNA cleavage.

Various biologically important phosphate esters may be hydrolyzed, or cleaved, according to the methods of the present invention, including phosphate monoester, diester and even triester linkages. Exemplary ester bonds that may be cleaved using matrix-supported texaphyrins are those present within physiologically important molecules, such as, nucleic acids, including, RNA from viral, bacterial and other pathogenic sources, as well as nucleic acid transcripts from oncogenes; mediators of metabolism, e.g., nucleotides such as ATP, ADP, AMP, cAMP, GTP, GDP, UDP, and cofactors such as NADH, NADPH, FAD, $FADH_2$ and UDP-glucose; phospholipids, such as phosphatidylcholine and phosphatidylethanolamine; other phosphate anhydrides; and a wide variety of assay substrates, such as p-nitrophenylphosphate ester.

In further embodiments, the present invention also provides advantageous methods for conducting a chemical reaction catalyzed by a lanthanide metal. These methods generally comprise preparing a matrix-supported metallotexaphyrin complex in which the texaphyrin is complexed to a lanthanide metal, and contacting the matrix-supported metallotexaphyrin complex with a composition comprising the substrates for the lanthanide metal-catalyzed chemical reaction. "Contacting" would generally be with a solution that includes the substrate molecule(s) for the reaction under conditions effective, and for a time period sufficient, to allow functional contact between the metal complexed texaphyrin and the molecule(s). Metallotexaphyrins complexed to La(III), Sm(III), Sm(II), Eu(III), Ce(III) or Dy(III) may be found to be particularly useful. These methods are suitable for the catalysis of reactions such as ester hydrolysis, amide hydrolysis, phosphate ester hydrolysis, acyl transfer, hydrogenation and polymerization.

Improved methods for MRI form another aspect of the invention, particularly as such methods may be used to locate a device or catheter within the body. In such methods, one would prepare a matrix-supported metallotexaphyrin complex comprising a paramagnetic metal ion, such as Gd(III), Cu(II), Ni(III), Co(II), Co(III), Fe(III) or Fe(III), then generally formulate this polymer-supported texaphyrin into a device and insert the device into an animal. By detecting the position of the paramagnetic metal ion within the animal, one would then be able to detect, monitor, adjust and/or retrieve the device. The use of Gd(III) is particularly preferred in such embodiments.

In further aspects, the invention provides new methods for light-induced singlet oxygen production using matrix-supported texaphyrins, optionally, in combination with diamagnetic metal cations such as Lu(II) or La(III). By subjecting a matrix-supported texaphyrin or texaphyrin diamagnetic metal complex to light in the presence of oxygen, singlet oxygen production is induced.

This may be used as a method for photodynamic tumor therapy (PDT). Here, one would generally contact a matrix-supported texaphyrin or texaphyrin diamagnetic metal complex with a composition suspected of comprising tumor cells and then photoirradiate the composition as it is contacted with the matrix-supported texaphyrin or texaphyrin diamagnetic metal complex. Photoirradiation is used in a sufficient quantity to induce singlet oxygen production at levels that are cytotoxic to the tumor cells. This is particularly suitable for use, ex vivo, in deleting tumor cells from the blood of patients that have, or are suspected to have, leukemia, so that the purged blood may be re-administered to the patient.

Another method of exploiting singlet oxygen formation using a matrix-supported texaphyrin is to deactivate a retrovirus or enveloped virus, such as HIV-1, HIV-2, HSV, SIV or FIV. Again, one would prepare a matrix-supported texaphyrin or matrix-supported texaphyrin diamagnetic metal complex; contact this with a composition suspected of comprising a retrovirus or enveloped virus; and then photoirradiate the composition in contact with the matrix-supported texaphyrin or texaphyrin diamagnetic metal complex to produce singlet oxygen in a quantity cytotoxic to any virus. In this way, viruses may be removed from blood and blood products suspected of comprising retrovirus or enveloped virus. This is useful not only in terms of rendering blood free from virus for use in transfusions, but also for use in rendering blood products and sera free from virus for use as growth media, e.g., in monoclonal antibody generation.

A further use of the matrix-supported texaphyrins involves the discovery that photosensitive texaphyrins catalyze the cleavage of a polymer of deoxyribonucleic acid. Cleavage is enhanced by the presence of oxygen, indicating that singlet oxygen or another oxygen by-product is the likely toxic agent. A photosensitive texaphyrin may be a diamagnetic metal texaphyrin complex or may be metal-free. The interaction between a matrix-supported texaphyrin-oligonucleotide conjugate and the complementary oligonucleotide is an example of antisense technology and allows cleavage of a polymer of deoxyribonucleic acid that is in the vicinity of the specific binding. The inherent biolocalization properties of texaphyrin further effect targeting of an antisense agent to lipophilic regions, especially tumors and atheroma, for example.

The term "texaphyrin-oligonucleotide conjugate" means that an oligonucleotide is attached to the texaphyrin in a 5' or 3' linkage or both types of linkages to allow the texaphyrin to be an internal residue in the conjugate. The oligonucleotide or other site-directing molecule may be attached either directly to the texaphyrin via a linker, or a couple of variable length. During catalysis, for example, the texaphyrin portion of a texaphyrin metal complex-oligonucleotide conjugate is placed in the vicinity of the substrate upon binding of the oligonucleotide to the targeted nucleic acid substrate. A "sapphyrinoligonucleotide conjugate" is referred to in the same way as described above for a texaphyrin-oligonucleotide conjugate except that the texaphyrin is replaced with a sapphyrin.

A couple may be described as a linker, i.e., the covalent product formed by reaction of a reactive group designed to attach covalently another molecule at a distance from the texaphyrin macrocycle. Exemplary linkers or couples are amides, amine, thioether, ether, or phosphate covalent bonds as described in the examples for attachment of oligonucleotides. In most preferred embodiments, oligonucleotides and other site-directing molecules are covalently bonded to the texaphyrin via a carbon-nitrogen, carbon-sulfur, or a carbon-oxygen bond.

The cleavage of DNA described herein is a photolytic cleavage. It is believed that the cleavage is not hydrolyric where a water molecule is added across a bond to break the bond, nor is the cleavage believed to be solely oxidative where an oxidation reaction in the absence of light causes breakage of the bond.

It will be apparent to one of skill in the art in light of the present disclosure that the site-specific cleavage of DNA has important ramifications in a variety of applications. Potential particular applications for this process include antisense applications; the specific cleavage and possible subsequent recombination of DNA; destruction of viral DNA; construction of probes for controlling gene expression at the cellular level and for diagnosis; and cleavage of DNA in footprinting analyses, DNA sequencing, chromosome analyses, gene isolation, recombinant DNA manipulations, mapping of large genomes and chromosomes, in chemotherapy and in site-directing mutagenesis.

The term "photosensitive" means that upon irradiation, texaphyrin effects either the generation of oxygen products that are cytotoxic or means that the texaphyrin is fluorescent, or both. Cytotoxic oxygen products may be singlet oxygen, hydroxyl radicals, superoxide, or hydroperoxyl radicals. The texaphyrin may be a diamagnetic metal complex or a metal-free species. Diamagnetic metals would include preferably, Lu(III), La(III), In(III), Zn(II) or Cd(II). Most preferably, the diamagnetic metal is Lu(III).

A further embodiment of the present invention provides a method of light-induced cleavage of a polymer of deoxyribonucleic acid. The method comprises the steps of contacting the polymer with a matrix-supported photosensitive texaphyrin and exposing the matrix-supported photosensitive texaphyrin to light for a time sufficient to cleave the polymer. In a preferred embodiment, the exposing step is carried out in the presence of oxygen. The texaphyrin may be a metal complex of texaphyrin, preferred metals are diamagnetic metals. The polymer may be a solution or a suspension of DNA or may be cellular DNA in vitro or in vivo. DNA is preferably cleaved over RNA.

Another embodiment of the present invention is a method for targeted intracellular DNA cleavage. The method comprises the introduction into a cell of a matrix-supported texaphyrin coupled to an oligonucleotide having complementary binding affinity for a targeted DNA, whereby cleavage of the targeted DNA is catalyzed by the matrix-supported texaphyrin. The DNA may be oncogene DNA or may be normal DNA which needs to be destroyed, for example, due to improper timing of expression. The oligonucleotide coupled to the matrix-supported texaphyrin may be DNA, a DNA analog, or an RNA analog oligonucleotide. The texaphyrin may be a free base texaphyrin or a metallated form of texaphyrin. The metal is preferably a diamagnetic metal, most preferably Lu(III).

A method for inhibiting the expression of a gene in an animal comprising the administration to the animal of a matrix-supported texaphyrin oligonucleotide-conjugate is a further embodiment of the present invention. The oligonucleotide may have complementary binding affinity for regulatory regions of the gene or for regions encoding exons or introns. The oligonucleotide may be complementary to either strand of the DNA or to the duplex DNA. A further embodiment of the present invention is a method for inhibiting the expression of a gene in a particular tissue of an animal comprising administering to the animal a matrix-supported texaphyrin having specificity for the tissue. The texaphyrin may have appended an oligonucleotide complementary to the target gene.

A further embodiment of the present invention is a matrix-supported texaphyrin conjugate wherein two or more separate matrix-supported texaphyrin complexes are attached to an oligonucleotide, one at the 3', one at the 5' end, and/or one or more at an internal residue. The texaphyrin may be metal free or may be metallated. A metal ion of each of the matrix-supported texaphyrin complexes may be the same or it may be different. Similarly, each of the matrix-supported texaphyrins may be different. Use of a dual texaphyrin complex-conjugate should effect the cleavage of DNA with increased efficiency due to the concerted activity of the metal complexes. For diagnosis and treatment purposes, the administration of such a matrix-supported conjugate with one texaphyrin complex having a diamagnetic metal species and the other having a paramagnetic species would allow binding, imaging, and cleavage, all effected by one conjugate. In this case, binding is effected by the oligonucleotide, imaging is accomplished by MRI due to the presence of the paramagnetic metal ion, and cleavage is accomplished by the photosensitive texaphyrin containing a diamagnetic metal cation. Therefore, the biodistribution and cellular penetration of the matrix-supported conjugate may be determined.

In terms of apparatus for use in phosphate ester cleavage, catalysis, ex vivo PDT, and DNA photocleavage, it is contemplated that the matrix-supported texaphyrins may be formulated into various columns, including HPLC columns; capillary electrophoresis tubes; and various other devices such as filters and large reaction vessels.

Although the present invention generally concerns polymeric matrices or solid-supports linked to texaphyrins, in certain other embodiments the invention provides for the linkage of further groups to a texaphyrin. TheSe include, for example, sugars, sugar derivatives, polysaccharides, metal chelating groups, alkylating agents, nucleobases, modified nucleobases, oligonucleotides, antibodies, hormones, steroids, steroid derivatives, amino acids, peptides, polypeptides, other texaphyrins and texaphyrin derivatives, rubyrin and rubyrin derivatives, sapphyrins and sapphyrin derivatives, polymeric sapphyrins, polymeric texaphyrins, and the like.

Other embodiments of the invention relate to expanded porphyrin, and particularly, texaphyrin derivatives that are polyhydroxylated and therefore water-soluble. Water soluble texaphyrins are particularly desirable where one would like to exploit the various surprising properties of these macrocycles in connection with human or animal applications. The nature of the polyhydroxylation is not believed to be particularly critical to achieving water solubility of a texaphyrin derivative, so long as at least two hydroxyl groups per macrocycle are incorporated into the structure. This is similar to sapphyrins, where the present inventors have found that the introduction of at least 1 or 2 hydroxyl groups per macrocycle was sufficient to achieve some degree of sapphyrin water solubility. This aspect of the invention is also important to the improved chromatographic and electrophoretic supports disclosed herein.

One means for introducing hydroxyl groups into a texaphyrin structure is simply through the addition of hydroxyalkyl substituents to the basic macrocyclic unit. Thus, exemplary polyhydroxylated texaphyrins are those that are modified to include structures such as hydroxymethyl, hydroxyethyl, hydroxypropyl, hydroxybutyl, dihydroxyalkyl, trihydroxyalkyl, or the like, at one or more R positions of the basic structure.

An alternative means of achieving polyhydroxylation is through the addition of sugar moieties such as a saccharide, polysaccharide, saccharide derivative or aminosaccharide, to the texaphyrin macrocycle structure. In an analogous case, it has been found that the addition of a single saccharide molecule to a sapphyrin macrocycle achieves a degree of water solubility. These structures are referred to broadly herein as texaphyrin- and sapphyrin-sugar compounds, conjugates or derivatives.

The nature of the sugar is not critical to the achievement of water solubility, and a non-exhaustive, exemplary list of sugars contemplated to be useful in this regard is set forth in Table 1. Of course, any sugar or modified sugar may be employed including sugars having additional phosphate, methyl or amino groups and the like. Moreover, the use of both D- and L-forms, as well as the α and β forms is also contemplated. However, it is contemplated that preferred sugars for use in accordance herewith will include, for example, glucose, glucosamine, galactose, galactosamine and mannose.

TABLE 1

Examples of Sugars and Sugar Derivatives

| | |
|---|---|
| Ribose | Fructose |
| Arabinose | Sorbose |
| Xylose | Tagatose |
| Lyxose | Fucose |
| Allose | |
| Altrose | Methylglucoside |
| Glucose | Glucose 6-phosphate |
| Mannose | |
| Gulose | N-Acetylgalactosamine |
| Idose | N-Acetylglucosamine |
| Galactose | Sialic Acid |
| Talose | Chitosan |
| Ribulose | Alginic Acid |
| Xylulose | |
| Psicose | |

For hydrolyzing nucleic acids, such as RNA, using a texaphyrin derivative, it is currently preferred to use a Eu(III)-texaphyrin, and most preferably a solid-supported Eu(III)-texaphyrin. RNA cleavage using Eu(III)-texaphyrins and solid-supported Eu(III)-texaphyrins is described herein in Example 14.

In further embodiments, the present invention relates to what are referred to as expanded porphyrin, and particularly, texaphyrin-nucleobase conjugates. As used herein, the term "texaphyrin-nucleobase conjugate" is intended to refer broadly to any conjugate formed by the covalent conjugation of any texaphyrin macrocycle to any nucleobase. The texaphyrin-nucleobase conjugates may also be attached to polymeric matrices or solid-supports, such as silica gel, glass, Merrifield resins, polyacrylamide, polystyrene, sepharose, agarose, clays, zeolites, plastics, biocompatible matrices and the like; to form a chromatography column, filter or medical device.

As used herein, the term "nucleobase" is intended to refer broadly to any moiety that includes within its structure a purine or pyrimidine, a nucleic acid, nucleoside, nucleotide, or any derivative of any of these. Thus, the term nucleobase includes adenine, cytosine, guanine, thymidine, uridine, inosine, or the like, bases, nucleotides or nucleosides, as well as any base, nucleotide or nucleoside derivative based upon these or related structures.

A particular example of useful nucleobases are the so-called antimetabolites, which are generally based upon the purine or pyrimidine structures. These compounds typically exert their biological activity as antimetabolites through competing for enzyme sites and thereby inhibiting vital metabolic pathways. However, in the context of the present invention, the inventors are employing the term "antimetabolite nucleobase" quite broadly to refer to any purine or pyrimidine-based molecule that will effect an anticellular, antiviral, antitumor, antiproliferative or antienzymatic effect, regardless of the underlying mechanism. Exemplary structures are shown in Table 2, including preferred conjugates such as purine or pyrimidine antimetabolites such as FU, AraC, AZT, ddI, ddC, xylo-GMP, Ara-AMP, PFA or LOMDP, and phosphorylated versions thereof.

Preferred compounds for conjugating to a texaphyrin include naturally-occurring purine or pyrimidine nucleobases, namely, cytosine, guanine, thymidine, adenine and uridine. Equally, such texaphyrin conjugates may include modified versions of any of these, such as the heterocyclic components of those nucleoside/nucleotide analogues listed in Table 2 and phosphorylated version of the compounds listed therein.

TABLE 2

Modified Nucleoside/Nucleotide Analogue
Anti-Metabolites

AraC
AraAMP
Azaribine
Azathioprine
Azauridine
AZT
Bromodeoxyuridine
Chlorodeoxyuridine
Cytarabine
Deoxyuridine
Dideoxycytidine ddC
DideoxyInosine ddI
Erythrohydroxynonyladenine
Floxuridine
Fluorouracil (5-FU)
Idoxuridine
LOMPD
Mercaptopurine
PFA
Thioguanine
Trifluoromethylde-oxyuridine
Xylo-GMP Also included within the invention are texaphyrin mononucleobase derivatives including chemically modified nucleobase such as "protected" bases. Protecting groups are used to protect reactive groups, such as amino and carboxyl groups, from inappropriate chemical reactions. Texaphyrin-nucleobase conjugates with protected bases include, for example, conjugates wherein one or more base has a protecting group, such as 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl or N-di-(4-methoxyphenyl)phenylmethyl on the amino group of the nucleobase.

Conjugation of a nucleobase to a texaphyrin derivative to form a mononucleobase texaphyrin conjugate may be via any of the R groups shown in Structure I. Conjugation of the two separate nucleobases to a texaphyrin derivative to form a dinucleobase texaphyrin conjugate may also be via any two of these R groups. Any of the texaphyrin mono-, di-, or oligo-nucleobase conjugates and derivatives, including both naturally-occurring nucleobases and modified nucleobases, may also be linked to a solid-support to form a matrix-supported texaphyrin composition.

In synthesizing nucleobase conjugates by the condensation of texaphyrin mono- and bis-acids with conveniently modified nucleobases, various spacers may be used. These include, for example, oligomethylene bridges with terminal amino, or hydroxy function, which allow formation of an amide or ester bond for the connection of the texaphyrin and nucleobase units. This bridge may also be modified, e.g., by the reduction of the amide bond to give the amine function. The present invention thus encompasses many possibilities for the connection of the same or different nucleobases to texaphyrin macrocycles.

It is contemplated that expanded porphyrin-nucleobase conjugates will have a wide variety of applications, ranging from the use of texaphyrin-derived compounds as agents for selectively delivering an associated, biologically active nucleobase to a particular body, or even subcellular, locale to the more general use in laboratory protocols concerned with nucleotides or oligonucleotides. For example, in the case of antimetabolite nucleobases and texaphyrins, it is contemplated that the texaphyrin-nucleobase conjugates will act to deliver the antimetabolite to subcellular sites through intrinsic biolocalization, or through a covalently coupled site-directed molecule, such as an oligonucleotide, peptide, or hormone, for example.

Expanded porphyrin-nucleobase constructs may employ only one nucleobase-containing substituent for each macrocycle; however, this is in no way a limitation upon the invention. For example, texaphyrin-nucleobase conjugates of the present invention may have any number of nucleobases or nucleobase oligomers or polymers attached. The choice of base would be generally governed by the application in which the conjugate was to be primarily used. Thus, it is contemplated that a texaphyrin-nucleobase conjugate with adenine will selectively bind thymidine, presumably through a hydrogen bonding of the two nucleotides. Furthermore, it is contemplated that polymers of texaphyrin-nucleobase conjugates can be constructed and used to bind oligo- or poly-nucleotides through complementarity with the sequence of bases "encoded" on the texaphyrin-nucleobase polymer.

The foregoing general structure could be exemplified by the formulas:

```
X—X—X—X—X—X—X, etc. or  X   X   X   X   X   X, etc.
|   |   |   |   |   |   |       |   |   |   |   |   |
N   N   N   N   N   N   N       N—N—N—N—N—N
|   |   |   |   |   |   |       |   |   |   |   |   |
Y—Y—Y—Y—Y—Y—Y           Y—Y—Y—Y—Y—Y
``` wherein X is the texaphyrin macrocycle, N is the conjugated nucleobase structure, and Y is the hydrogen bonded poly- or oligonucleotide.

Alternatively, it is contemplated that texaphyrins of the present invention may serve as a carrier for polymers of nucleobases, wherein the nucleobase polymers are attached covalently to the texaphyrin macrocycle, such as might be exemplified through the structural designation:

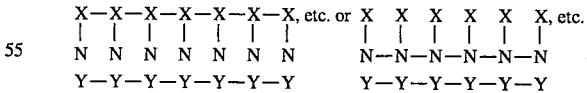

X-N-N-N-N-N-N-,etc.,

Y-Y-Y-Y-Y-Y- wherein X is a single texaphyrin macrocycle, and N is a selected oligomeric or polymeric nucleotide or other nucleobase, and Y is a hydrogen bonded poly- or oligonucleotide.

Such structures would be useful in a number of contexts'. In terms of texaphyrins, they are currently envisioned to be useful in RNA hydrolysis. In terms of sapphyrins, they may be used as specific carriers for taking complementary nucleotides into cells. The complementary nucleotides could be structures such as antisense molecules, including C-5 propyne-containing antisense oligonucleotides, designed to inhibit the transcription, translation or both, of a given gene or construct. Alternatively, they could be coding for "sense" strands of DNA which encode an entire gene, a functional protein domain, or any polypeptide, peptide, or fragment thereof. Such constructs may be used in in vitro molecular biological embodiments or in gene-transfer protocols in which the DNA is intended to act as a template for the production of proteins or peptides such as normally-functional or therapeutically-important proteins and peptides.

Chemically speaking, any number of nucleobase structures can be attached to a texaphyrin macrocycle. The ultimate number of such residues that are attached will, of course, depend upon the application. Where one intends to employ such a structure to purify complementary nucleotides, one may well desire to employ a structure having a polymer of at least 10 or so bases attached. However, for other applications, it may be convenient to design and employ texaphyrin-nucleobase constructs employing from one to three nucleobases per single macrocycle. Moreover, the nature of the intended use will dictate the number of attachment points there are on the texaphyrin macrocycle for attaching nucleobase moieties. Thus, while it may typically be the case that a single attachment site will suffice for most applications, for certain particular applications those of skill may find it particularly advantageous to attach various nucleobases at various of the subcomponents of the macrocycle.

A. Purification Protocols

There is currently a significant need for improved nucleotide- and oligonucleotide-binding compounds for use in connection with various laboratory techniques, both in clinical and research embodiments. For example, oligonucleotides are currently purified using polyacrylamide gel electrophoresis (PAGE) which is time-consuming, uses toxic materials, and is low-yielding. Ion exchange columns can, on a limited basis, sometimes separate oligonucleotides containing 40 or fewer residues. However, this process is also generally unsuitable as, for example, severe conditions such as elution at pH 2.7, are often required. The availability of a new column material, or improved functionalized glass capillaries, for use in chromatographically or electrophoretically separating nucleotides and oligonucleotides would thus represent a significant breakthrough in this area.

The inventors' surprising discovery that expanded porphyrins, such as rubyrin, sapphyrin and texaphyrin, recognize and bind phosphates, also lead the inventors to reason that such expanded porphyrins would be ideal for use in laboratory techniques to separate and purify nucleotides and oligonucleotides. This is a very important area to both scientists and clinicians as nucleotides, natural and synthetic oligonucleotides play critical roles in modern biotechnology. Oligonucleotides are used, for instance, as hybridization probes in blot analyses, primers for PCR amplification, and for sitespecific mutagenesis. Furthermore, in areas that are under FDA jurisdiction, oligonucleotide-derived products are currently being used as probes for the detection of genetic diseases and for proviral HIV, the causative agent of Acquired Immunodeficiency Syndrome (AIDS)[2]. They are also being considered as potential chemotherapeutic agents, both directly, i.e., in gene therapy, and in an antisense fashion.[3]

All the above applications for using oligonucleotides require oligonucleotide materials of impeccable purity (often greater than >99.99%)[4]. Such purity, however, is not so easy to obtain using existing technology[4,5]. Presently, gene products and other oligonucleotide-type materials are purified using polyacrylamide gel electrophoresis (PAGE). This approach suffers from the drawbacks of being time-consuming, requiring toxic materials, and is painfully manpower-sensitive and low-yielding[2].

Liquid chromatography, high performance liquid chromatography (HPLC), and high performance affinity chromatography (HPAC)[6,7] using specialty silica gels are currently used to separate biological molecules. Indeed, silica gel phases with bonded groups, such as linear hydrocarbons, amino groups, cyano-groups, carboxylic amides and amino acids are all known. Unfortunately, few if any, of these phases are efficacious for the efficient, high-yielding separation of nucleotides and oligonucleotides.

Those that work best for this purpose are ion exchange columns which, on a limited basis, can sometimes separate oligonucleotides containing 40 or fewer residues. However, this technique still suffers from several limitations, not least that it requires severe conditions, including elution at pH 2.7, for routine operation[8]. The use of high concentration buffers (greater than 1M), and gradients which often include formic acid or formamide, also limits the half lives of ion exchange columns. Furthermore, commercially available hydroxyapatite columns are limited for low pressure only (up to 719 psi). Reverse-phase columns are designed for pressures up to 5000 psi. However, this separative technique is based on hydrophobic interaction and, because there is not a specific interaction for phosphorylated species, it is not surprising that effective separation is not generally achieved.

Recently, Takemoto et al. reported a new type of stationary phase in which purine and pyrimidine bases were bonded to the silica gel[9]. With this support, base-pairing interactions between the nucleic acid base pairs and the modified silica gel were expected to improve resolution in nucleic acid separation. Although such stationary phases were used to separate nucleic acid free-bases, purine alkaloids, nucleosides, and mono- and oligonucleotides, this approach unfortunately had least success with oligonucleotide separation, which is the most important area. Thus, there was still a critical need for improved solid-supports that would effectively separate nucleotides and oligonucleotides.

The inventors realized that for a solid-support to be most useful in such embodiments, it must not only separate similar nucleotides and oligonucleotides from one another, it must do so rigorously and correctly based on chain length or size. Unfortunately, prior to the present invention, there were no suitable phosphate chelating agents that made this an achievable goal for use in either HPLC or electrophoretic separation systems.

B. Texaphyrin-Substituted Silica Gels and Merrifield Resins

In certain embodiments, the matrix-supported expanded porphyrins of the present invention will be bonded, texaphyrin-substituted glass capillaries or silica gels that will serve as specific phosphate- or nitrate-chelating solid-supports. These may be used in the chromatographic and electrophoretic separation of nitrates, phosphates and phosphorylated species, including nucleotides, oligonucleotides, and DNA or RNA molecules including gene fragments, and will be suitable for both analytical and preparative HPLC applications.

These aspects of the invention therefore encompass a full range of texaphyrin-modified stationary phases. When the bonded stationary phase or polymer is silica gel, the resulting products will be used for medium to high pressure applications. For low pressure applications, organic polymer based texaphyrins, for example, modified Merrifield resins, will be prepared using the same basic strategy. In all cases, the wide range of intrinsic variation, imparted via additional groups and the texaphyrin R groups will afford the opportunity to prepare stationary phases capable of separating a wide range of phosphorylated species.

To date, a first generation texaphyrin-substituted silica gel has been prepared as described in Example 4. With this silica gel, a 3.2 mm×30 mm HPLC column was packed (by Alltech Inc). Then, in the initial series of studies, this column was used to separate various, adenosine-derived nucleotide mono-, di-, and triphosphates with significant success.

The ability to separate nucleotide mono-, di-, and triphosphates from cell extracts has long been a challenging task. Most of the commercially available HPLC columns provide less than adequate separation of di-from triphosphates. However, such separations are instrumental in determining cell energy charge (eq. 1), which is used as an indicator of cell health in the study of many diseases.

$$\text{Adenylate Energy Charge} = \frac{[ATP] + 0.5\,[ADP]}{[AMP] + [ADP] + [ATP]} \qquad (1)$$

A great advantage afforded by these aspects of the invention is that different numbers of texaphyrin molecules may be introduced per polymer unit simply by varying the molar ratio of texaphyrin derivative to the number of the groups bonded on the polymer surface. The inventors, therefore, also propose to vary the micromolar concentration of texaphyrin used per gram of silica gel in order to control the retention times and to influence peak shape characteristics. Straightforward modifications such as these will thus allow such systems to be used in both analytical and preparative modes.

In addition to the separation of nucleotides, as described above, the inventors envision the separation of oligonucleotides using a matrix-supported metallotexaphyrin having little or no hydrolyric or cleavage activity towards oligoribonucleotides or oligodeoxyribonucleotides. Gadolinium is a preferred metal for this separation, however other metals such as lanthanum, lutetium, neodymium and yttrium are expected to be effective.

Thus, it is clear that these new chromatographic supports are suitable for use in analyzing and purifying a large number of critical products, including small molecule antiviral agents and oligonucleotides such as hybridization probes and primers. They represent a marked advance over existing technology including PAGE, HPLC, HPAC, ion exchange columns and purine and pyrimidine base-bonded silica gels, and are expected to find many immediate applications in DNA-related biotechnology and medicine.

Such matrix-supported texaphyrins are also contemplated for use in separating very large RNA or DNA molecules such as gene fragments and antisense constructs. In order to achieve separation of higher order oligonucleotides, the inventors envision that various elution-related parameters, such as, e.g., flow rate, buffer strength, and texaphyrin-to-silica loading level, may be optimized so as to achieve the best possible separations. Second and/or third generation polymer-supported expanded porphyrins may also be prepared for use in connection with RNA or DNA separation and purification.

C. Second and Third Generation Texaphyrin Solid-Supports

The preparation of improved, i.e., second and third generation, texaphyrin solid-supports is also contemplated. Such new systems will be designed to separate phosphorylated compounds based upon other specific binding modes in addition to the phosphate recognition provided by the moiety. For example, hydrophobic interaction separation is contemplated, and can be provided by modifying the length of alkyl chains employed. Recognition mediated by Watson-Crick hydrogen bonding interactions is also contemplated. This may be achieved by using expanded porphyrin-nucleobase conjugates, by appending nucleobases onto the solid-support itself, or by using a combination of both methods. Introduction of aromatic ring (phenyl, substituted phenyl) or amino or silanol groups gives the possibility for $\pi$—$\pi$ stacking interactions.

The second generation stage of this new synthetic development may be considered to be the stage of long chain alkyl addition. Long chain alkyl groups will thus be introduced onto the surface of the texaphyrin-substituted silica-gel. This will result in columns that will combine the properties of both reverse phase separation and texaphyrin-based phosphate chelation and ion exchange. Further, in light of the existing theories of HPLC, the inventors contemplate using appropriate synthetic modifications to optimize the retention characteristics of the columns so that they separate selectively any desired length of oligonucleotide and/or gene fragment.

The yet superior third-generation systems contemplated by the inventors are those in which the stationary phases will combine the best features of three different known modes of separation: hydrogen bonding, electrostatics, and reverse phase hydrophobicity. This will be achieved by using various different substituents on both the texaphyrin molecules and on the stationary phase material itself.

For example, in certain embodiments, these groups may be varied so as to introduce a nucleobase or nucleobase analog. Such nucleobase-bearing systems are expected to act in conjunction with the combined texaphyrin electrostatic and reverse phase hydrophobic interactions described above. Thus, by this triple combination, it is expected that the resultant solid phase will be able to separate nucleotides and oligonucleotides not only on the basis of charge and length but also on the basis of nucleic acid type. Such phases, of course, would prove to be of tremendous value in applications involving the analysis and purification of gene fragments since these are often of similar size but of very different chemical (i.e., nucleic acid) composition.

These same third generation phases would also be of tremendous benefit in the separation and analysis of AZT phosphate, dideoxycytidine phosphate, and other prodrugs used in the asymptomatic treatment of HIV and other viral infections. Here, in particular, it would be of significant value to have access to an analytical method that would allow one to distinguish the active phosphorylated nucleotide analogs from naturally occurring phosphorylated products, such as AMP or GMP, since this would allow for facile, on-line clinical analysis.

D. Texaphyrin Substituted Capillary Electrophoresis

In still further embodiments, the inventors also contemplate using polymer-supported texaphyrins in connection with capillary electrophoresis (CE). In CE, unlike HPLC, no solid silica or Merrifield resin support is used. Rather, differential adherence to the glass surface of a capillary is used to effect separation. Thus, in this embodiment, texaphyrin-modified glass capillary surfaces will be prepared and used for improved CE resolution. In these embodiments, the polymer will be an untreated glass capillary rather than silica gel. Since glass is chemically similar to silica gel (both are silicate-derived), the preparation of a range of modified glass surfaces can be straightforwardly achieved in light of the present disclosure.

Such texaphyrin-glass constructs may be used to separate natural and synthetic nucleotides and oligonucleotides. Here, as above, the best combination of complexed metals and substituent groups needed to effect any given type of separation will be determined. The information gained using silica gels will be applied in these considerations and supplemented by further straightforward studies. It is expected that this will lead to a significantly improved new CE system. To highlight the utility of such a system, the inventors contemplate carrying out a Sanger sequencing of pBR322 using fluorescently labeled dideoxy nucleotides (Applied Biosystems Inc.). Since an entire range of fragment sizes is produced here, this will allow the superiority of the new texaphyrin-based approach to be quickly demonstrated.

E. Polymer-supported Texaphyrins in Purification Protocols

As described above and in the detailed examples, the inventors designed and constructed texaphyrin-based supports and used them to achieve--separation-of nucteotides, thus overcoming many of the existing drawbacks described above. Similar methods using a polymer-supported texaphyrin are envisioned to be of use purifying plasmid DNA, as described in Example 7D.

Another technical area in which significant improvements could be made is in oligonucleotide analysis. For example, automated gene sequencing is currently carried out using either radio- or fluorescent-labeled nucleic acid gel electrophoresis. This technique is limited by the requirement for either slab or tubular polyacrylamide gels. An alternative approach, currently being considered on a research basis, is to use capillary electrophoresis. Unfortunately, this is limited when it comes to achieving separations based purely on electrostatics and oligomer size. Texaphyrins linked to glass capillary columns, as disclosed herein, provide new devices and methods that allow for such separation. This, therefore, represents a significant improvement in this area.

A further utility of polymer-supported expanded porphyrins, i.e., texaphyrins and sapphyrins is their use as tools in the removal of phosphate- or nitrate-containing environmental contaminants from ground water, soil, foodstuffs, and the like. The sapphyrins and texaphyrins have different binding mechanisms that may render one more useful in certain embodiments. For example, one may prefer to use a sapphyrin polymer-support to remove phosphates or nitrates from solutions. Metallotexaphyrins conjugated to solid-supports offer a unique and distinct way of effecting the recognition and purification of anionic and neutral substrates. However, despite the different mechanisms, both texaphyrin and sapphyrin columns will likely bind and remove a variety of anionic compounds, with texaphyrins also binding to and being able to purify neutral molecules, such as sugars, including sugars present within the blood stream.

Texaphyrin and sapphyrin matrix-supports may be employed to analyze and separate pesticides such as Dichlorovos, Phosphamidon, Diazanon, and Parathion, herbicides and fungicides, many of which contain organophosphorus compounds. Texaphyrin-substituted gels and columns may even be employed in the rapid detection and analysis of organophosphorus chemical warfare agents, allowing them to be disposed of where necessary.

Anionic species such as nitrates, phosphates and various metals elements are major sources of environmental pollution. In marine environments, an excess of nitrate can cause an imbalance of the water chemistry and lead to the formation of excess algae which can threaten the balance of the entire ecosystem. Similarly, excess nitrates in soil can lead to poor growth conditions for crops. Therefore, a system to remove excess nitrates, phosphates and metals from environmental sources would be of great benefit for retaining the delicate balance in these ecosystems.

F. Matrix-Supported Texaphyrins in Catalytic Schemes

The ability to produce a wide range of matrices is dependent on the ability to synthesize active catalysts. These catalysts must be able to convert the appropriate monomers, such as ethylene or styrene, to the desired polymeric materials.

Lanthanide texaphyrin complexes have potential as active polymerization catalysts. There are several reasons for this. First, the texaphyrin ligand is essentially planar with the metal being slightly above the plane defined by the five chelating nitrogens, a geometry that allows access to the metal from either side of the macrocycle. Second, because the total coordination number of a metallotexaphyrin complex is high while that of the ligand itself is low, the texaphyrin complexes should allow substrates such as alkenes or dihydrogen to be easily accommodated. Finally, the catalysts proposed herein will have two potential active sites. This is unlike any of the previous lanthanide based catalytic systems, which have been limited to cyclopentadienyl type ligands and is important because, presumably, the catalytic cycle for either polymerization or hydrogenation includes coordination of the substrate followed by a series of insertion steps. The cyclopentadienyl complexes by contrast are limited to one alkyl substituent being available for use in catalytic cycles, with this single alkyl being constrained in a crowded pocket. The texaphyrin complexes, on the other hand, will have two alkyl substituents in a, sterically speaking, rather open environment. Further, the macrocyclic ligand will disfavor formation of dimers which occur in the $C_5Me_5$ based catalysts, which may enhance the rates of the catalytic reaction.

The present invention now allows the lanthanide texaphyrin (txph) complexes, as linked to solid-supports, to be used as the basis for preparing a new set of potential polymerization and hydrogenation catalysts. These compounds may now, for the first time, be employed in heterogeneous catalysis, as described below.

As lanthanide coordinating ligands par excellence, the texaphyrins, when supported on solid matrices, provide a source of unparalleled Lewis acidity as a result, primarily, of the fact that trivalent cations of the lanthanide series are far better Lewis acids than cations of the more common metals. This Lewis acidity, in turn, allows for the use of texaphyrins, either free in solution or supported on supports, in a range of catalytic applications. These range from such standard catalytic applications of Lewis acidity as acyl transfer, ester hydrolysis, and amide hydrolysis to more sophisticated embodiments as phosphomono- and phosphodiester hydrolysis.

In all cases, however, the critical catalytic step is thought to involve, in a mechanistic sense, the binding of a carbonyl or heteroatom-containing carbonyl-like oxygen lone pair to the coordinated texaphyrin metal center. This binding, in accord with the widely accepted principles of Lewis acid catalysis, will serve to activate the already acidic carbonyl carbon or heteroatom (e.g., phosphorus) for subsequent attack by a nucleophile. When this latter nucleophile is provided by water, hydrolysis ensues; when it is provided by an alcohol, amine, or other standard nucleophilic organic group, acyl transfer results. Thus these catalytic systems, as normal for all catalysts (principle of microscopic reversibility) can be used to both make and break bonds.

From a practical point of view, the general procedure will always be the same: Bring into contact with the solid-supported Lewis acidic texaphyrin (e.g., polymer-supported Gd(III)texaphyrin), a particular desired substrate (ester, amide, phosphomonester, phosphodiester, etc.) in the presence of the chosen nucleophile ($H_2O$, ethanol, diethylamine, etc.). Reaction will then occur with all the advantages of normal heterogeneous catalysis (site isolation, easy product purification, facile catalyst recycling, etc.) resulting in a high yield of the desired product, be that one derived from hydrolysis or acyl transfer.

The stability of the matrix-supported texaphyrin complexes allows them to be subjected to harsh conditions, such as organic solvents and elevated temperatures, without breakdown of their structure. This property imparts a particular usefulness to the range of polymer-supported metallotexaphyrins and, for example, allows them to be used as catalysts in various embodiments where the use of a biological catalyst, such as an enzyme, is impossible due to their instability and/or temperature sensitivity.

On the other hand, Samarium (III) complexes are envisioned to be particularly useful due to the relative ease of characterization compared to the remaining lanthanide complexes. For instance, samarium complexes typically have narrow line widths in NMR spectra even though the metal center is paramagnetic. Therefore $^1H$ and $^{13}C$ NMR spectra may be used as standard characterization tools. In fact, this is the case for $Sm(txph)(NO_3)_2$ which exhibits an $^1H$ NMR spectra resembling that of a diamagnetic complex. Conversely, the Gd(III) complexes with their known high relativity- inducing abilities will be useful for MRI applications. For both the Gd(III) and Sm(III) and other complexes, other characterization techniques will include IR, UV/vis, mass spectroscopy, elemental analysis and, when appropriate, single crystal X-ray diffraction analysis. Polymeric or oligomeric materials obtained from these catalysts will be examined via standard polymer analyses including mass spectroscopy, GC/MS, gel permeation chromatography as well as those techniques listed above.

When attached to a solid-support, particularly one of a biocompatible nature, these new paramagnetic materials will be of unique use as MRI-detectable catheters. These, in turn, will be of use for medical diagnosis applications. These, or similar, solid-supported materials will also be of use as heterogeneous Lewis acidic catalysts with the usual advantages of site isolation, product purity, and catalyst recovery that would accrue from such heterogeneous catalysts.

G. Matrix-Supported Texaphyrins in MRI

Non-invasive techniques for the diagnosis of human disease are extremely valuable tools in the practice of modern medicine. One of the most important new techniques available uses magnetic resonance (MRI) to image tissues and organs within the body. This provides an advantage over the use of X-rays, which have harmful side-effects. A complication of this technique arises when the patient has a catheter, implant or other internal device which needs to be located within the body. At the present time, the majority of these devices are composed of materials that do not produce an adequate signal when subject to MRI. Therefore, catheters and other devices composed of a material which is highly detectable during MRI scans would be of great medical utility.

Gadolinium(III) complexes derived from strongly binding anionic ligands, such as DTPA and DOTA, are being developed for use in MRI. Indeed, [Gd•DTPA]⁻ is undergoing clinical trials in the United States for possible use in enhanced tumor detection protocols. Nonetheless, the development of other gadolinium(III) complexes with greater kinetic stability, superior relativity, and/or better biodistribution properties was still a desirable goal until recent times. The provision of water-soluble texaphyrins for use in MRI enhancement, as described in U.S. Pat. No. 5,256,399, incorporated herein by reference, addressed this particular need. However, it did not provide a solution to the problem of locating a catheter or medical device using an MRI scan.

This is an important application provided by the present inventors: that of using a metallotexaphyrin as a primary component of a catheter or device for enhanced visibility during MRI. This concept is more fully developed in Example 10.

H. Matrix-Supported Texaphyrins in PDT

Acquired immunodeficiency syndrome (AIDS) and cancer are among the most serious public health problems facing our nation today. AIDS is a fatal human disease that has now reached pandemic proportions. Cancer, in spite of some very significant advances in diagnostics and treatment in recent years, remains the third leading cause of death in this country. Finding better ways to detect, treat, and reduce the transmission of these disorders are thus research objectives of the highest importance.

One of the more promising new modalities currently being explored for use in the control and treatment of tumors is photodynamic therapy (PDT). This technique is based on the use of a photosensitizing dye, which localizes at, or near, the tumor site and, when irradiated in the presence of oxygen, serves to produce cytotoxic materials, such as singlet oxygen ($O_2(^1\Delta g)$), from otherwise benign precursors (e.g. ($O_2(^3\Sigma_g-)$)) Much of the current excitement associated with PDT derives from just this property: In marked contrast to current methods (e.g. conventional chemotherapy), in PDT the drugs themselves can (and should) be completely innocuous until "activated" with light by an attending physician. Thus, a level of control and selectivity may be attained which is not otherwise possible.

Singlet oxygen is also believed to be the critical toxic species operative in experimental photosensitized blood purification procedures. This very new application of photodynamic therapy is of tremendous potential importance: It shows promise of providing a safe and effective means of removing enveloped viruses such as HIV-1, herpes simplex (HSV), cytomegalovirus (CMV), various forms of hepatitis-inducing virus, as well as other opportunistic blood-borne infections (e.g. bacteria and malaria plasmodium) from transfused whole blood. Given that AIDS is currently an ineffectively treated and usually fatal disease, the benefit of such a blood purification procedure would be of inestimable value.

AIDS infections do still occur as a result of blood transfusions. Unfortunately, banked blood components are essential products for the practice of modern medicine and as a result this method of transmission is not likely to be precluded by simple changes in lifestyle. Rather, a means to ensure that all stored blood samples are free of the AIDS virus (and ideally all other blood-borne pathogens) should be developed. To a certain extent, this can be accomplished by screening the donors' histories and carrying out serologic tests. At present, however, the serologic tests for HIV-1 are insufficient to detect all infected blood samples, in particular, those derived from donors who have contracted the disease but not yet produced detectable antibodies. In addition, new mutants of the AIDS virus have been detected; some or all of which may escape detection by current means. Thus, an antiviral system is needed which removes any form of HIV-1 from stored blood. This is particularly important since a stored blood sample from one infected donor could potentially end up being administered to several different patients, in, for instance, the course of pediatric care.

Texaphyrins and texaphyrin metal complexes are effective as photosensitizers for the generation of singlet oxygen. As described in U.S. Pat. No. 5,272,142, incorporated herein by reference, metallotexaphyrins can be used for the inactivation or destruction of tumors as well as for the prophylactic treatment and removal of human immunodeficiency virus (HIV-1), and other viral contaminants from blood. The metallotexaphyrins with Cd(II), Sm(III), La(III), Lu(III) have been studied, and the Cd(II) was found to be effective against certain types of leukemia cells. However, there are still many existing drawbacks to PDT.

The present invention forms a basis for a novel treatment of diseases, such as leukemia, where the fluid from the body can be removed from the patient and exposed to PDT by use of a column which contains a polymeric supported texaphyrin. The treated fluid can then be reintroduced to the patient without fear of contamination from the texaphyrin. This avoids any unnecessary exposure of the patient's whole system to the effects of the photodynamic therapy.

The matrix-supported texaphyrins of the present invention also allow for the deactivation of retroviruses and enveloped viruses in biological fluids, such as blood and blood products, using columns, filters or such like. These methods are advantageous as the fluids may be passed over the column. This may result in improved kinetics, but the very evident advantage is, again, that the treated fluid can be readily recovered and introduced to the patient without fear of contamination from the texaphyrin.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

PREPARATION OF SAPPHYRIN POLYMERS

For the preparation of certain polymers, sapphyrins with ethylene units could be used, as prepared by the elimination of acetoxy derivative, as well as sapphyrin bis acid, sapphyrin diamino and dihydroxyderivatives. Sapphyrins bearing covalently attached nucleobases could also be used for the polymerization reactions. Example 10 of co-pending application, PCT publication WO 94/09003, is specifically incorporated herein by reference to supplement the present example.

Radical polymerization may be catalyzed by dibenzoylperoxide, or bisazaisobutyronitril in inert solvent at temperature 120°–200° C.

Polycondensation reaction:
3,12,13,22-Tetraethyl-8,17-bis(carboxyethyl)-2,7,18,23-tetramethylsapphyrin (1 mmol) and 1,1'-carbonyldiimidazole (1.1 mmol) were mixed in diphenylether for 1 hour, then 3,12,13,22-tetraethyl-8,17-diaminoethyl-2,7,18,23-tetramethylsapphyrin (1 mmol) was added and reaction heated at 190°–250° C. for 2 hours. After cooling, dichloromethane was added, polymeric sapphyrin structure (where X=NH) was filtered off, washed with water (50 ml) and methanol (50 ml).

Polymeric sapphyrin was obtained also with using sulfolan, hexamethylphosphortriamide as a solvent. The reaction could be also carried out without solvent. The same procedure was used for the sapphyrin dialcohol as a starting compound for the reaction with sapphyrin diacid.

EXAMPLE 2

SYNTHESIS OF POLYMER SUPPORTED SAPPHYRINS

The new chromatographic bonded phases that are the subject of these aspects of the present invention were prepared in two steps. In the first, a phosphate thioether recognition unit was connected (via amide, ether, thioether, or NH bonds) with silica gel. This was followed, as a second step, by protection of residual silanol groups on the silica gel surface using a variety of silylating reagents (from $C_1$ to $C_{18}$). The density of coverage for the covalently bonded recognition groups on the silica gel was controlled by the amount of expanded porphyrin, or guanidinium derivatives (in mmol) that was attached to 1 g of the starting silica gel. Elemental analysis data, namely comparison of the % C and % N in the starting material and the product, provided a measure of the ratio of phosphate receptor (in μM) to 1 g of silica gel. Solid state $^{31}P$ NMR spectra also provided a unique tool for the detailed study of the mechanism of phosphate binding.

Example 11 of co-pending application, PCT publication WO 94/09003, is specifically incorporated herein by reference to supplement the present example.

EXAMPLE 3

GENERAL SILYLATION PROCEDURE

For the separation of highly polar phosphorylated species on both analytical and preparative scale, the surface of silica gel must be modified by a silylation procedure. This procedure basically converts most, if not all, the free silanol groups (—Si—OH) to —Si—O—Z type residues, where Z is an alkyl chain, or aryl substitution ($ARCO_2$—, ARCO—). Silylation reagents which have been employed are those of type $Z_2SiCl_2$, $ZSiCl_3$, and $Z(CH_3)_2SiCl$, where Z is an alkyl residue with 1 to 18 carbon atoms in it or an aryl (phenyl, pentafluorophenyl) substituent.

For the silylation of the bonded silica gels in this invention, the present inventors have used the following procedure: Introduction of the $C_1$, $C_8$, $C_{12}$, and $C_{18}$ groups by reaction of mono and trichlorosilanes with suspended bonded silica gel in an organic solvent (dry dichloromethane, dichloroethane, benzene, toluene, xylene, or pyridine and 2,6-lutidine was used directly as a solvent) either directly or in the presence of organic bases such as pyridine or 2,6-lutidine, in a temperature range of 25° C.–150° C. for the preparative HPLC phases, the corresponding triflates were used for silylation.

Example 12 of co-pending application, PCT publication WO 94/09003, is specifically incorporated herein by reference to supplement the present example.

EXAMPLE 4

SYNTHESIS OF TEXAPHYRIN-BONDED SILICA

The synthesis of texaphyrin-bonded silica gel was accomplished by amide bond formation between activated (Eu) texaphyrin carboxylic acid (carbodiimide method) and amino-substituted silica gel.

A. Synthesis of (Eu) Texaphyrin Acid EuT2B1 $(O(CH_2)_3CO_2H)$

The $sp^3$ texaphyrin derivative T2B1.HCl, (having $O(CH_2)_3CO_2H$ as an R substituent on the B portion of the molecule, 0.694 g, 1 mmol, see U.S. Pat. No. 5,252,720 for T2B1 structure) was dissolved in 80 ml of dry methanol. Eu $(OAc)_3.H_2O$ (0.329 g, 1 mmol) was added, followed by triethylamine (0.5 ml). The reaction mixture was heated at reflux with the reflux condenser open to the air for 6 hours, with the progress of metallation being followed by visible spectroscopy. The methanol solvent was evaporated off under reduced pressure to give a dry, dark solid that was washed with dichloromethane for 2 hours under conditions of vigorous stirring.

The product was filtered off, redissolved in MeOH (25 ml), and the solution was treated with zeolite (a procedure for removing free europium salt). The product 4a was then twice precipitated from methanol by adding diethylether. The resulting dark green solid was then collected and dried under high vacuum overnight. The yield was 91.0%.

Characterization data: Elemental analysis for $C_{38}H_{44}N_5O_5Eu$. 2(OAc) (F.W. 920.855) calc. 54.78% C, 5.47% H, 7.61% N; found 54.46% C, 5.50% H, 7.55% N. FAB HR MS: For $C_{38}H_{43}N_5O_5Eu$ calc. 802.24626; found 802.247752. UV-Vis (EtOH, $\lambda$max): 420,469,760 nm.

B. Procedure for the Synthesis of Texaphyrin-Bonded Silica Gel (Eu)-texaphyrin carboxylic acid 4a (M=Eu, $^1R$=CH$_2$OH, n=3, 0.50 mg) was dissolved in a mixture of dichloromethanedimethylformamide (1:1,5 ml) and cooled to 0° C. The carbodiimide derivative was then added (EDC, 100 mg), followed by 1-hydroxybenzotriazole. The resulting reaction mixture was kept for 45 minutes at this temperature and slowly added to the 3-aminopropyl silica gel (1 g of 3-aminopropyl silica gel, Sigma Company, 1.0 mmol N per gram), suspended in dry dichloromethane (25 ml) containing 0.5 ml of dry pyridine. The reaction mixture was stirred at 0° C for 30 minutes and then at room temperature for 3 days. The product was filtered off, washed with dichloromethane (30 ml), methanol (50 ml), water (100 ml), methanol (50 ml), and dichloromethane (30 ml). The product 4b was dried (giving 1.035 g) and used for further derivatization, namely direct silylation, or 1) introduction of other functional groups and then 2) silylation.

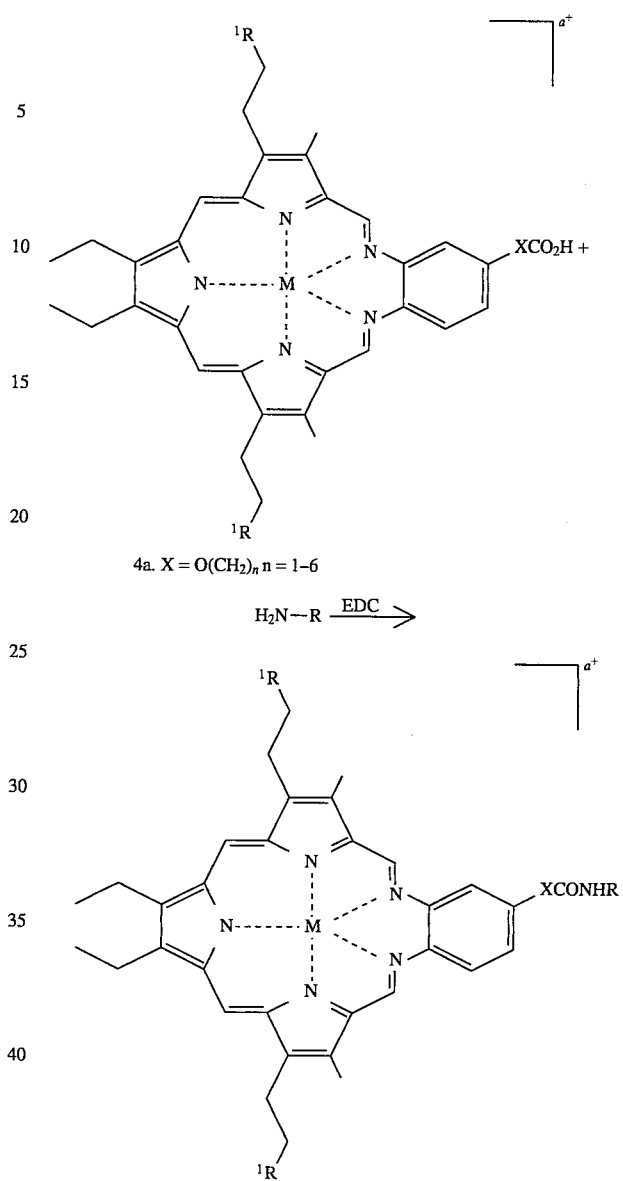

4a. $X = O(CH_2)_n$ n = 1–6

4b. M = trivalent metals such as Y(III), In(III), Ln(III), where Ln = Lanthanide; $H_2N$—R represents an amino-functionalized solid support C. Silylation procedure (Eu) texaphyrin-silica gel as described above (1.0 g) was suspended in dry dichloromethane (30 ml) containing dry pyridine (3 ml). To this solution, a solution of dimethyldichlorosilane (2 ml) in dry dichloromethane (10 ml) was then slowly added before the resulting reaction mixture was allowed to stir for days at 30° C. The product was isolated by filtration and washed as described above. The yield was 1.04 g.

Also used in the silylation procedure was trimethylsilylimidazole in dichloroethane and other silylation agents, as described in co-pending application, PCT publication WO 94/09003, specifically incorporated herein by reference for the purposes of describing further silylation procedures.

EXAMPLE 5

SECOND AND THIRD GENERATION TEXAPHYRIN SOLID-SUPPORTS

The preparation of improved second and third generation texaphyrin solid-supports may be achieved in many ways. For example, in one stage of the synthetic development, long chain alkyls may be introduced onto the surface of the texaphyrin-substituted silica-gel. This is contemplated to result in second-generation columns that will combine the properties of both reverse phase separation and ion exchange.

Examples 15 and 16 of co-pending application, PCT publication WO 94/09003, are specifically incorporated herein by reference for the purposes of supplementing the present example in terms of the preparation of second and third generation matrix-supported texaphyrins.

Improved, third generation texaphyrin solid-supports may also be prepared. For example, third-generation systems may be prepared in which various different substituents on both the expanded porphyrin molecules and on the stationary phase material itself are chosen to impart the desired groups and properties to the resultant material.

In one case, nucleobase-bearing systems may be generated which are expected to be able to separate nucleotides and oligonucleotides not only on the basis of charge and length but also on the basis of nucleic acid type. The use of nucleobase-bearing systems to hydrolyse RNA oligonucleotides with sequence specificity is also contemplated. The introduction of aryl substituents give the possibility for improved separation based on phosphate chelation and $\pi$—$\pi$ stacking. Any substituent for multiple type separation may be introduced by acylation, akylmethylation on free amino groups and/or by silylation with phenyl (substituted phenyl), silyl reagents or arylmethylation of OH groups.

More specifically, the following text describes the preparation of partially texaphyrin-functionalized 3-aminopropyl silica gel suitable for the introduction of additional functions. This sorbent was prepared for the second and third generation of columns, with the intention to leave a certain number of amino groups free (unbound to texaphyrin) for the subsequent binding of other types of recognition units. The latter functional groups include both hydrogen-bond recognition units for nucleobases, aromatic residues capable of effecting $\pi$—$\pi$ stacking interactions with the pyrimidine or purine rings of nucleotides, as well as, in certain embodiments, other expanded porphyrins such as texaphyrins and sapphyrins.

Also, for phosphodiester hydrolytic purposes an imidazole ring can be easily introduced by reaction with amino-protected (e.g. 1-BOC-L-Histidine). A positive charge near the texaphyrin macrocycle can also be introduced by reaction with, for example, L-arginine methylester.

EXAMPLE 6

SEPARATION OF NEGATIVELY CHARGED SPECIES USING A TEXAPHYRIN SOLID-SUPPORT COLUMN

The present example sets forth various procedures that are contemplated to be of use in connection with the polymer-supported texaphyrins of the present invention. Example 14 of co-pending application, PCT publication WO 94/09003, is specifically incorporated herein by reference for the purposes of supplementing the present example in terms of the separation of negatively-charged species using expanded porphyrin matrix-supports.

Columns using the new bonded texaphyrin materials are stable in aqueous buffers from pH 4.0 to pH 9.0, with operation at pH 5.0 being preferred in certain embodiments. They are also stable to normal organic solvents and the packings are mechanically rigid due to their silica gel backbone. Indeed, the chemical and mechanical stability of such new columns makes them suitable for use over long periods of time without loss of resolution. Moreover, columns made from the presently described supports do not compress at high pressure and flow rates. The use of surface modified spherical silica gels results in products for use in medium to high pressure applications. For low pressure applications, organic polymer based solid-supports, for example, modified Merrifield resins, may be used.

It is contemplated that the effectiveness of separation using these new stationary phases will be far superior to those currently used. Also, the lifetimes of the columns are long because only very mild elution conditions are required: low concentration of buffer at neutral pH. Usually, isocratic (i.e., non gradient) conditions are sufficient for the separation even for very complicated mixtures. This makes the analysis of a series very fast and there is no need for column equilibrium after each analysis.

These advantageous features allow for the rapid and efficient separation of nitrates, phosphates and different phosphorylated species, such as nucleotides, mono-, di- and triphosphates, oligonucleotides, DNA and RNA fragments, phosphosugars, phosphoproteins and organophosphorus compounds, using the expanded porphyrin-based solid-supports of this invention.

Texaphyrin columns are prepared using a standard column packing procedure. In this context, the columns are slurry-packed in methanol or acetone, followed by a wash with water. An HPLC pump that generates a solvent flow of about 10 ml/min at 300–400 bar is used.

A. Separation of mono-, di-, and tri-phosphorylated nucleotides using a sapphyrin solid-support Using the first generation of the sapphyrin-substituted silica gel the inventors were able to successfully separate adenosine and its mono-, di-, and tri-phosphorylated nucleotide forms.

The results of the HPLC separation of adenosine, mono-, di-, and tri-phosphates using the first sapphyrin-modified silica gel were very striking. Commercially obtained adenosine, AMP, ADP, and ATP were prepared by dissolving in 5 mM tris (hydroxymethyl) aminomethane buffer at pH 7.0. An adenosine, AMP, ADP, and ATP mixture, (20 μl), was loaded onto and eluted off the sapphyrin-modified silica gel using an isocratic buffer of 100 mM dibasic ammonium phosphate buffer at a pH of 7.0 and a flow rate of 0.2 ml/min (or, in another study, 500 mM buffer and a flow rate of 1.0 ml/min). The wavelength of 260 nm was monitored and results were confirmed with retention times and UV-visible spectrum obtained from samples of individual compounds.

It is clear that there is a striking difference between the sharp peaks using the new sapphyrin-based technology and the unresolved broad band obtained with a more conventional column.

B. Separation of Mono-, Di-, and Polyanionic Species Using a Metallotexaphyrin Solid-Support The present inventors have demonstrated that silica-bound lanthanide texaphyrins, specifically, europium(III)

texaphyrin can effectively separate mono-, di-, and polyanionic species under isocratic HPLC conditions.

Two separate studies were performed to determine whether the silica-bound europium texaphyrin would be specific to different anions. HPLC columns were packed with the silica-bound europium texaphyrin of Example 4 by Alltech, Inc. (Deerfield, Ill.) at the request of the inventors and according to standard column packing procedures. Benzoic acid, benzene sulfonic acid, diphenylphosphate, and phenylphosphate were injected into a 3.2 mm (i.d.)×30 mm HPLC column. The mobile phase used was 50/50 (v/v) methanol/10mM sodium acetate, 20 ml, (pH=7). The results are given in Table 3.

TABLE 3

| Substrate | Time (min.) |
| --- | --- |
| Benzoic Acid | 5.9 |
| Benzene Sulfonic Acid | 6.0 |
| Diphenyl Phosphate | 6.1 |
| Phenyl Phosphate | 16.8 |

As Table 3 shows, the type of anion is less relevant than the charge of the anion. Phenyl phosphate at a pH of 7 is a dianionic species, while benzoic acid, benzene sulfonic acid, and diphenyl phosphate are monoanionic.

To confirm this result, 5'-adenosine mono-, di-, and triphosphate as well as 3', 5' cyclic adenosine monophosphate were injected onto the HPLC column. The results are summarized in Table 4.

TABLE 4

| Substrate | Time (min.) |
| --- | --- |
| Adenosine | 1.2 |
| 3',5'-cyclic AMP | 1.3 |
| 5'-AMP | 4.1 |
| 5'-ADP | 10.1 |
| 5'-ATP | 30.2 |
| ApA | — |

As shown in Table 4, the monoanionic cyclic AMP eluted at nearly the same time as the neutral adenosine. The other phosphate derivatives showed a much higher affinity for the solid phase than the monoanionic cyclic AMP.

There was no indication that the dinucleotide, ApA, had come off the column even after 8h. As a control, the same solution was tested on a commercial 3.2 mm (i.d.)×100 mm reverse phase column. ApA was eluted after 30 minutes using a similar flow rate and buffer as used with the "texaphyrin column." Eutexaphyrin can hydrolyze phosphodiesters in solution (U.S. Ser. No. 08/227,370, incorporated by reference herein), and it is expected that the ApA was hydrolyzed by the EuTXP.

The present data show that the expanded porphyrin, texaphyrin, when metallated with a lanthanide metal, was able to effectively separate adenosine, AMP, ADP and ATP. Since crystal structures of dysprosium texaphyrin show that phosphate anions ligate to the dysprosium via axial binding, the inventors believe that the separation is via axial ligand binding to the lanthanide metal in the texaphyrin macrocycle. Varying the metal in the macrocycle is expected to achieve varying degrees of selectivity between anions.

When a higher order nucleotide, ApA, was used, the silica-bound texaphyrin hydrolyzed the phosphodiester bond between the nucleotides. Varying the metals in the solid-support bound texaphyrin macrocycle will vary the rate of hydrolysis and the specificity of hydrolysis.

C. Separation of 2-, 3-, 4-, 5-, 6-, 7-, 8-, and 9-mer Oligonucleotides

Using the first generation sapphyrin substituted silica gels, the inventors were able to successfully separate 2-, 3-, 4-, 5-, 6-, 7-, 8- and 9-mer oligonucleotides.

Results of the HPLC separation of commercially obtained adenosine-derived oligonucleotides using the first sapphyrinmodified silica gel were significant. Samples of 2-, 3-, 4- and 5-mers of polydeoxyadenylic acid were prepared by dissolving in 5 mM of tris (hydroxymethyl)aminomethane at pH 7.0. This mixture (20 μl) was loaded onto and eluted off the column using an isocratic buffer of 100 mM dibasic ammonium phosphate at pH 7.0 and a flow of 0.35 ml/min. The wavelength of 260 nm was monitored and results were confirmed with retention times and UV-visible spectrum obtained from samples of individual compounds.

The results obtained with the sapphyrin-based methodology were very impressive. There was a marked difference between the sharp, distinct peaks observed and the broad, unresolved peak obtained when the same mixture was run through a control column with no sapphyrin. Furthermore, in addition to separating out the oligonucleotides in this supposedly pure mixture, higher and lower order impurities were also observed.

Results of the HPLC separation of longer commercially obtained adenosine-derived oligonucleotides using the first sapphyrin-modified silica gel were also impressive. A sample of a mixture of 2-, 3-, 4-, 5-, 6-, 7-, 8- and 9-mers of polydeoxyadenylic acid was loaded onto and eluted off the column using 100 mM dibasic ammonium phosphate at pH 7.0 and a flow of 0.35 ml/min. The wavelength of 260 nm was monitored and results were confirmed with retention times and U/V-visible spectrum obtained from samples of individual compounds.

These results are also striking, and effective separation of all species was achieved. Clearly, all of these results are remarkable, particularly as various impurities, not known to be present in the commercially available mixture, were identified, the presence of which was later confirmed at source (Sigma Chemical Co.).

D. Separation of Nitrates

The binding of nitrates is contemplated to be of significance in removing nitrates from water samples, including, for example, drinking water, particularly for babies, and also water in fish tanks and aquariums—there is currently no way of achieving this. Of course, removal of both nitrates and phosphates, such as alkylphosphonates and detergents, from contaminants of waste water or ground water is also contemplated.

EXAMPLE 7

MATRIX-SUPPORTED TEXAPHRYINS FOR USE IN PURIFICATION PROTOCOLS

The present example details further embodiments in which the matrix-supported texaphyrin compositions are contemplated to be particularly useful.

A. Purification of Anionic Species

Metallotexaphyrins conjugated to solid-supports offer a unique new way of effecting the recognition and purification of anionic substrates. This is because they possess, coordinated within their central cores, large metal cations that necessarily (by definition) are Lewis acidic and hence able to bind, as apical or axial ligands various Lewis basic entities, including those that are negatively charged. However, the degree of this Lewis acid-to-Lewis base interaction is a function not only of the particular metal center coordinated to the central, pentaazatexaphyrin core, but also of the Lewis base itself, since the latter could vary in the degree of basicity or ligand donor strength as well as in size and steric accessibility. Thus, when allowed to interact in a chromatographic sense with a given texaphyrin, maintained on a solid-support, individual Lewis basic materials will be retained differentially.

Texaphyrins linked to solid-supports therefore provide highly selective means for separating species from solutions of different anionic materials. When a solution is contacted with the texaphyrin-based solid-support and subjected to standard elution procedures, distinct components will be released at different rates. They can then be collected as small eluent fractions to allow for the obtainment of the various components of the original anion mixture in a partially or completely purified fashion.

Here, it is readily apparent that this purification methodology would be equally applicable to thin layer chromatography (TLC), high pressure liquid chromatography (HPLC), batch separations (where bulk washings rather than constant elutions are used), and electrophoretic applications; in all cases it is the now disclosed substrate-to-texaphyrin interactions, rather than the specifics of the chromatographic separation, that are considered to be key.

B. Purification of Neutral Species

Metallotexaphyrins, as is apparent from inspection of numerous crystal structures[1,13], also bind neutral entities as apical ligands provided that these entities are electron rich (i.e., Lewis basic). Thus, texaphyrins conjugated to solid-supports can also be used to effect the chromatographic or electrophoretic separation of neutral, Lewis basic entities. Here, as above, it is the fact that different neutral substrates differ in their ligation ability (because of differences in Lewis basicity, sterics, etc.) that makes such separations possible. Specifically, modulations in interactions (with the texaphyrin metal centers) will correlate with differences in retention and/or elution behavior such that one desired substrate can be separated out from a mixture of similar, but still different, substrates and hence obtained in purified form.

C. Purification of Oligonucleotides and Related Materials

The separative purification of oligonucleotide and other polyphosphorylated substrates represents a specific embodiment of the above Lewis base-to-texaphyrin based procedure. Here, however, the major advantage that the presently disclosed approach would provide over the currently available methods is an ability to separate ostensibly similar materials on the basis of total phosphate number. This is because oligonucleotides, for instance, of different length would present to the texaphyrin-bearing surface a number of total interactive axial ligands that differ absolutely. Thus, the degree of interaction between the texaphyrin surface and the substrate in question, i.e., an oligonucleotide of different length. As a consequence, the order of elution would be different in a chromatographic or electrophoretic sense and a means for differential purification established.

D. Purification of Plasmid DNA

An important application of lanthanide(III) texaphyrin (LnTx) functionalized polymers involves their utility in the separation of plasmid DNA from RNA, protein, and other cellular contaminants. Current protocols describe procedures for lysis of bacterial cells and provide a source of crude plasmid DNA (e.g., Sambrook, Fritsch, and Maniatis, *Molecular Cloning*, 2nd Edition, Cold Spring Harbor Laboratory Press, 1989, 1.21–1.39)[11] which is then further purified either by treatment with pancreatic RNase and precipitation with polyethylene glycol (cf. Sambrook, 1.40–1.41) or by equilibration centrifugation in cesium chloride-ethidium bromide gradients (cf. Sambrook, 1.42–1.43). However, the former procedure is inappropriate for larger (>15 kb) DNA plasmids (cf. note in Sambrook 1.37) while the latter procedure is labor and time consuming and employs the toxic chemical ethidium bromide.

The use of matrix-supported texaphyrins presents a novel alternative method of purification, whereby unwanted RNA contaminants are removed by virtue of their susceptibility to hydrolysis by the lanthanide complexes. Treatment with the solid-supported LnTx catalyst therefore results in the degradation of RNA to mononucleotides, which are readily removed using a standard ethanol precipitation. Unwanted protein is also readily removed by virtue of its relatively low affinity for the solid-supported LnTx. An example of a typical purification protocol is described immediately below.

The crude nucleic acid pellet, obtained by the boiling, SDS, or alkaline lysis methods (Sambrook, 1.34–1.39), is resuspended in 3 mL of Tris EDTA buffer, pH 8.0. An appropriate amount of, e.g., silica bead supported LnTx is added to this solution, the suspension vortexed, and incubated in a heat block at greater than 37° C. for a period of time sufficient to effect complete hydrolysis of the RNA. The suspension is then cooled, washed into an eppendorf pipette tip to form a small column using Tris-EDTA buffer, and washed briefly to remove remaining protein. The purified DNA is then eluted from the solid-supported LnTx using a sodium phosphate buffer. The resulting DNA is precipitated using one-tenth volume of 3M sodium acetate, pH 5.4 and three volumes of ethanol. The supernatant is decanted, the DNA pellet washed with 70% ethanol, and allowed to air-dry. The purified DNA is resuspended in any desired buffer.

EXAMPLE 8

MATRIX-SUPPORTED TEXAPHYRINS FOR USE IN CATALYSIS

The present example sets forth various ways in which matrix-supported metallotexaphyrins may be employed to catalyze a variety of chemical transformations.

A. Catalysis of Phosphodiester Hydrolysis

Solid-supported lanthanide texaphyrins provide a unique means of catalyzing the hydrolysis of phosphodiesters. The Lewis-acidic lanthanide metals coordinated within the texaphyrin bind the phosphate, thus activating the phosphate towards hydrolytic cleavage. Thus, a suspension of the solid-supported lanthanide texaphyrin can be treated with a solution of a phosphodiester (such as RNA) resulting in the hydrolysis of the phosphodiester. The catalysts may then be easily removed by a simple filtration. Thus, products may be easily separated from the catalysts.

An alternative method would be to develop continuous flow processes. In such a process, the phosphodiester solution is passed over a stationary catalyst bed. The phosphodiester interacts with the texaphyrin complexes resulting in hydrolysis of the diester. Product is then collected as the solution exits the catalyst bed.

These applications are also pertinent to the hydrolysis of phosphomonoesters. Thus, using the procedures described above the phosphate group of a phosphomonoester may be completely removed. These processes are of particular interest when applied to site-selective RNA hydrolysis.

The fact that europium texaphyrin attached to a solid-support can catalytically hydrolyze phosphodiester bonds at neutral pH was demonstrated in Example 4. Therefore, two-phase catalytic hydrolysis of phosphodiesters is possible. The inventors envision using silica bound texaphyrin for phosphodiester hydrolysis of polynucleotides (DNA or RNA) by injecting them onto a column or stirring them in a round bottom flask, and extracting the hydrolyzed nucleotides. Gadolinium- and dysprosium-texaphyrin have both been shown to hydrolyze phosphodiester bonds by the present inventors.

B. Catalysis of Polymerization

A stirred suspension of solid-supported lanthanide texaphyrin alkyl complexes may be treated with an appropriate monomer solution (ethylene, styrene, acetylene, phenylacetylene, etc.) resulting in polymer formation. Additional monomers (different from the initial monomer) may be added to this solution resulting in a block polymer. After complete polymerization has occurred the catalyst may be removed by filtration resulting in a purified polymer suitable for a variety of applications including household plastics or machine parts.

C. Catalysis of Hydrogenation

A hydrogen-saturated solution of alkene will be stirred with a suspension of the solid-supported lanthanide texaphyrin hydride complexes under a hydrogen atmosphere. The alkene will be hydrogenated to the corresponding alkane. The catalyst may then be removed by a simple filtration step resulting in a purified alkane suitable as a feed stock for the petroleum and chemical industries.

EXAMPLE 9

MATRIX-SUPPORTED TEXAPHYRINS FOR RACEMATE RESOLUTION

The present example describes the use of matrix-supported texaphyrins as chiral sorbents for HPLC. By the introduction of a chiral unit into the texaphyrin periphery, a sorbent for racemate resolution can be generated. Specific examples of chiral groups are D-glucopyranosyl, glucosamine, L-amino acids, such as L-alanine, or L-phenylalanine residues, oligopeptides, oligosaccharides and chiral binaphthyl systems.

The resultant chiral matrix-supported texaphyrins could be used for D,L-aminoacid separation, as well as for the separation of chiral phosphates, such as synthetic nucleotide monophosphates with modified ribose units, phospholipids, phosphoproteins, phosphorylated saccharides, and the like. These same polymer-supported texaphyrin chiral sorbents may be also used to effect catalytically a range of enantiotopic reactions, from chiral phosphate ester hydrolysis to stereoselective polymer genesis.

The following describes two general procedures for the coupling of carboxy-substituted chiral texaphyrins with an amino-functionalized solid-support in DMF or a water-DMF mixture.

A. Using 1,1'-Carbonyldiimidazole as a Coupling Reagent 1 mol. eq. of carboxylated texaphyrin was dissolved in dry DMF, 1.1 mol eq of 1,1'-carbonyldiimidazole was added and stirred under argon for 4 hours. Then the amino-component (1 mol eq.) was dissolved in a water-pyridine mixture (10:0), or in a buffer of pH 8.5 or higher (this is needed for successful coupling), and slowly added to the solution of activated carboxy-component. The reaction mixture was stirred at room temperature for 1–5 days or at 37° C. for 24 hours. During this period, the reaction could be followed by HPLC analysis. The work up includes evaporation at high vacuum, filtration of product, and washing of product.

B. Using Carbodiimide as a Coupling Reagent

Texaphyrin acid (1 mole. eq.) was dissolved in dry DMF and the solution cooled to 0° C. for 1 hour. The reaction mixture was then stirred at room temperature for 2–5 days, with the course of the reaction being followed by HPLC. The product was isolated by filtration and washing.

EXAMPLE 10

MATRIX-SUPPORTED TEXAPHYRINS FOR USE IN MRI

This example sets forth various ways in which matrix-supported metallotexaphyrins may be used in medical devices, such as catheters, to enhance visibility during magnetic resonance imaging.

As disclosed in U.S. Pat. No. 5,252,720, incorporated herein by reference, nonlabile Gd(III) complexes of hydroxy-substituted texaphyrins are useful contrast agents for MRI applications. Rats bearing subcutaneously implanted methylcholanthrene-induced fibrosarcomas in their left flanks (n=4) have been studied for imaging purposes, where results showed that the T2B2 gadolinium texaphyrin complex is a hepatic, renal and tumor-specific contrast agent. The agent was found to have relatively low toxicity in rodents. Tumor enhancement persisted for up to 28 hours. After this initial showing of utility in MRI, the inventors have developed the concept of using polymer-supported texaphyrins in other aspects of MRI, as set forth below.

In connection with the present example, U.S. Pat. No. 5,256,399 is also specifically incorporated herein by reference for the purposes of supplementing the present example where it concerns the use of texaphyrins in methods for MRI enhancement and in methods for detecting neoplastic tissues.

The ability to image internal body structures and diseased tissues non-invasively within a patient's body has become indispensable to the practice of modern medicine. A variety of such non-invasive imaging techniques exist, including x-ray imaging, ultrasonic imaging, x-ray computed tomography, emission tomography, and the like.

MRI can provide two-dimensional sectional images through a patient, providing color or gray scale contrast images of soft tissue, particularly for imaging tumors, edema, infarcts, infections, and the like. In addition to high quality, magnetic resonance images are particularly desirable since they do not expose the patient to harmful radiation.

However, patients undergoing magnetic resonance imaging often have catheters, tubes, implants, and other devices present within their bodies, and the precise anatomical locations of such devices can be of substantial clinical importance. Unfortunately, most catheters and many other devices are composed of materials, such as organic polymers, which do not produce adequate signals for detection by magnetic resonance imaging techniques. In particular, most polymeric catheters are not clearly discernible on magnetic resonance images unless they are surrounded by tissue that has a high signal intensity, in which case they leave a dark void on the image.

It is therefore highly desirable to provide catheters and other medical devices that have enhanced detectability when viewed using MRI regardless of the nature of the surrounding tissue. Here, it is contemplated that a texaphyrin complexed to an imaging ligand, such as Gd(III), and then linked to a catheter or device would be of great use in providing a high contrast image when viewed under MRI. Texaphyrins may be linked to catheters and devices by the same basic synthetic methodology that is employed, and described herein, to link texaphyrins to any other polymeric matrix.

The ions used for MRI may be any metal ion that displays paramagnetic properties and that binds to a texaphyrin, with exemplary transition metal cations including Gd(III), Cu(II), Ni(II), Co(III), Co(II), Fe(III), and Fe(II), with Gd(III) being preferred.

The polymeric materials particularly suitable for use in such catheters and devices include, for example, polyethylene, polyurethane, polyvinyl chloride, nylon, latex, silicone rubber, halogenated polyethylenes (e.g., polytetrafluoroethylene (PTFE) and other Teflon® materials), organosilicones (e.g., Silastic® materials) and biocompatible ceramics.

After linking the metallotexaphyrin to the polymeric material, the combination would then be formed into a tube, or shaped device, by conventional techniques, such as, e.g., injection molding or extrusion at elevated temperatures. Suitable extruders utilize polymeric materials and, by applying heat and pressure, form the materials to a continuous length of tubing having a desired diameter and wall thickness. The metallotexaphyrins of this invention may be incorporated throughout such tubes uniformly, or may be located only in a portion of the tube, such as a distal portion, or in a plurality of circumferential bands, e.g., axially spaced apart along the tube. Provision of such lengths and/or bands of paramagnetic ions can be achieved by periodically introducing the paramagnetic-texaphyrin complex into the polymeric material. As a further alternative, the paramagnetic ions can be provided along an axial line or strip of the flexible tubing, e.g. by introducing the texaphyrins into the extruder at one circumferential region of the tube as it is extruded.

These aspects of the invention are contemplated to be useful for modifying conventional catheters, feeding tubes, drainage tubes, shunts and other medical or veterinary devices that have component tubes. It is also suitable for use in generating improved interventional devices, such as those used for suturing and/or biopsy, and all devices that may be temporarily introduced into an animal's or patient's body, lumen or tissue. Texaphyrins may also be used to modify portions or components of permanently implantable devices, such as joint and other prostheses, breast implants, pacemakers, drug injection ports, pediatric intercardiac devices and even drug delivery devices, where it is desirable that the presence and location of the device be readily discernible during subsequent magnetic imaging procedures.

EXAMPLE 11

MATRIX-SUPPORTED TEXAPHYRINS AS INTERNAL RADIOACTIVE SOURCES

This example sets forth various ways in which matrix-supported metallotexaphyrins may be used in medical devices, including the types of catheters described immediately above, as part of radioimmunodiagnostics (RID) and radiosensitization therapy (RIT) protocols. It should be cautioned that all known uses of radioligands are not without their drawbacks and side-effects, and the same is true for the polymer-supported texaphyrins described herein.

Radioisotopes play a central role in the detection and treatment of neoplastic disorders. The more stable, polymer-supported texaphyrins of the present invention may be employed in radiosensitization and therapy (RIT), where the radiometal of interest must be bound and retained under physiological conditions. The potential damage arising from "free" radioisotopes, released from the complex, can be very serious. The advantage of a chelate, and particularly, a polymer-supported texaphyrin metal complex, that does not allow for metal release is clear.

For the purposes of imaging, an ideal isotope should be readily detectable by available monitoring techniques and induce a minimal radiation-based toxic response. In practice, these and other necessary requirements implicate the use of a γ-ray emitter in the 100 to 250 KeV range, that possesses a short effective half-life (biological and/or nuclear), decays to stable products, and, of course, is readily available under clinical conditions. To date, therefore, most attention has focused on $^{131}$I($t_{1/2}$=193 h), $^{123}$I($t_{1/2}$=13 h), $^{99m}$Tc($t_{1/2}$=6.0 h), $^{67}$Ga($t_{1/2}$=78 h) $^{111}$In($t_{1/2}$=67.4 h) which come closest to meeting these criteria.

Texaphyrin forms a kinetically and hydrolytically stable complex with In(III); such a ligand system may be elaborated and serve as the critical core of a matrix-supported texaphyrin conjugate for use in $^{111}$In-based radioimmunodiagnostics. Although not proposed for immediate clinical use, it is expected that a matrix-supported texaphyrin, e.g., a highly directable, small catheter, could be employed to deliver a radiotherapeutic insult to the center of a solid tumor that is not readily targeted by agents present in the blood. Texaphyrins having electron donating groups on the 2, 7, 12, 15, 18 and/or 21 positions of the present invention are particularly suited for this application due to their enhanced stability. A texaphyrin complexed to $^{90}$Y may be administered in combination with another texaphyrin complexed to a diamagnetic metal for photodynamic tumor therapy, for example, to achieve a synergistic killing of malignant cells.

EXAMPLE 12

MATRIX-SUPPORTED TEXAPHYRINS FOR USE IN PHOTODYNAMIC THERAPY

This example sets forth the uses of matrix-supported metallotexaphyrins in photodynamic therapy (PDT), as may be used, for example, to kill certain types of leukemia cells and to inactivate viruses.

A. Viral Inactivation by Matrix-Supported Texaphyrins

One example of the utility of the present invention is the use of matrix-supported texaphyrins for photon-induced deactivation of viruses and virally-infected or potentially-infected eucaryotic cells. U.S. Pat. No. 5,252,720, incorporated herein by reference, teaches that unsupported texaphyrins may be used to inactivate peripheral mononuclear cells and enveloped viruses. The columns of this invention are contemplated for use in inactivating viruses such as Herpes Simplex Virus Type 1 (HSV-1), HIV-1, HIV-2, FIV, SIV, and the like.

Texaphyrins having electron donating substituents in the 2, 7, 12, 15, 18 and/or 21 positions of the macrocycle, as shown in structure I and described in PCT application PCT/US95/01996, incorporated herein by reference, are expected to be more effective photosensitizers for the destruction of free enveloped viruses such as HIV-1, virally-infected peripheral mononuclear cells, as well as leukemia and lymphoma cells.

The novel treatment methods made possible by the matrix-supported texaphyrin technology include those in which fluid from the body is removed from the patient and exposed to PDT by use of a column which contains a matrix-supported texaphyrin. The treated fluid may be reintroduced into the patient.

The matrix-supported texaphyrins may also be used to remove functional viruses, such as HSV and HIV, from biological fluids, such as blood and plasma, or used as an additional control measure to ensure that blood samples do not contain viruses before storage or transfusions.

B. Photodynamic Therapy for Tumors

U.S. Pat. No. 5,252,720, incorporated herein by reference, demonstrates that La(III)B2T2 texaphyrin is phototoxic to murine mammary carcinoma cells in vitro and to murine adenocarcinoma tumor masses in Balb/c mice in vivo.

Improved, novel treatment methods made possible by the present matrix-supported texaphyrin invention include those in which fluid from a cancer patient is removed and exposed to PDT using a column that contains a polymer-supported texaphyrin. The treated fluid will then be re-introduced into the patient. This is particularly suitable for purging tumor cells from the blood of patients with leukemia.

EXAMPLE 13

TEXAPHYRIN SUBSTITUTED GLASS CAPILLARIES

Matrix-supported expanded porphyrins may be prepared in which the matrix is a glass capillary, for example, as may be used in capillary electrophoresis (CE). As glass is chemically similar to silica gel (both are silicate-derived), the preparation of modified glass surfaces may be achieved generally as described herein. The preparation of texaphyrin modified 3-amidosubstituted glass and texaphyrin modified arylamine glass would be essentially as described in Example 17 of co-pending application, PCT WO 94/09003, that is specifically incorporated herein by reference for the purposes of supplementing the present example in terms of the preparation of second and third generation matrix-supported texaphyrins.

EXAMPLE 14

SYNTHESIS AND INTERACTIONS OF TEXAPHYRIN-OLIGONUCLEOTIDES

PCT publication WO 94/29316 is incorporated by reference herein for methods relating to texaphyrin-metal-complex-mediated ester hydrolysis. U.S. Ser. No. 08/310,501 is incorporated by reference herein for methods relating to texaphyrin mediated photocleavage of a polymer of DNA.

A. Metallotexaphyrins with Amine, Thiol or Hydroxy-Linked Oligonucleotides

Amides, ethers and thioethers are representative of linkages that may be used for coupling oligonucleotides to texaphyrin metal complexes. Oligonucleotides functionalized with amines at the 5'-end, the 3'-end, or internally at sugar or base residues, are modified post-synthetically with an activated carboxylic ester derivative of the texaphyrin complex. Alternatively, oligonucleotide analogues containing one or more thiophosphate or thiol groups are selectively alkylated at the sulfur atom(s) with an alkyl halide derivative of the texaphyrin complex. Oligodeoxynucleotide-complex conjugates are designed so as to provide optimal catalytic interaction between the RNA or DNA phosphoester backbone and the matrix-supported texaphyrin-bound lanthanide cation(s).

Oligonucleotides are used to bind selectively compounds which include the complementary nucleotide or oligo or polynucleotides containing substantially complementary sequences. As used herein, a substantially complementary sequence is one in which the nucleotides generally base-pair with the complementary nucleotide and in which there are very few base pair mismatches. The oligonucleotide will generally be large enough to bind probably at least 9 nucleotides of complementary nucleic acid. A general method for preparing oligonucleotides of various lengths and sequences is described by Caracciolo et al. (1989)[12].

In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to coupled is reacted with the free hydroxyl of a growing nucleotide chain derivatized to a solid-support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base. Oligodeoxynucleotides or their phosphorothioate analogues may be synthesized using an Applied Biosystem 380B DNA synthesizer (Applied Biosystems, Inc., Foster City, Calif.).

B. Hydrolysis of Monoesters by Lanthanide (III) T2B2 Texaphyrin

This section provides an example of the utility of the present invention in the hydrolysis of monoesters, in particular, the hydrolysis of UpU, cUMP, 3'-UMP and 2'-UMP. Described are results from studies using the lanthanide (III) T2B2 texaphyrin (U.S. Pat. No. 5,252,720, incorporated by reference herein). Using the synthetic methodology of the present invention, a matrix-supported lanthanide (III) T2B2 texaphyrin would be constructed and used as described hereinbelow for the unsupported complex. It is contemplated that the matrix-supported version would function essentially as the free version, but would provide the many additional advantages associated with being attached to a column.

Cytosine, uridine, uridine-2' and 3'-monophosphate disodium salt (2'-UMP and 3'-UMP), uridine-2',3'-cyclicmonophosphate sodium salt (cUMP), and uridylyl(3'→5') uridine ammonium salt (UpU) were purchased from Sigma (St. Louis, Mo.) and used without further purification. All solutions, unless otherwise stated, were prepared from a stock solution of 5.0 mM N-(2-hydroxyethyl) piperazine-N'-ethanesulfonic acid (HEPES), in Milli-Q purified water, adjusted to pH 7.0. Solutions were stored and reactions conducted in RNAse free plastic vials further sterilized by heating at 120° C. for 20 minutes in an autoclave. All kinetic runs were thermostated at 37° C. in a water bath.

High-performance liquid chromatography (HPLC) was performed on a Waters 501 equipped with a Waters model 440 absorbance detector, monitoring at 254 nm. A YMC, Inc., USA ODS-AQ column (150 mm×4.6 mm I.D.) was used. Satisfactory separation was achieved with an isocratic gradient (10 mM $NaH_2PO_4$ adjusted to pH 5.6 with 1% methanol) with a flow rate of 1.0 ml/min. A Beckman DU-7 spectrometer was used to confirm the concentrations of EuB2T2 txp.

$Eu(NO_3)_3$. In the control, the reaction solutions were prepared by diluting 100 µl of UpU (2.94 mM), 25 µl of $Eu(NO_3)_3$ (3.5 µm), and 100 µl of cytosine (0.423 mM), as internal standard, in 375 µl of 5.0 mM HEPES solution. The reactions were carried out as for EuB2T2 txp. The pseudo-zero order rate constant for the control reaction was determined to be $k=(2.2\pm0.8)\times10^{-4}$ mM/h.

EuB2T2 txp. In a typical kinetics analysis, the reaction solutions were prepared by diluting 100 µl of UpU (2.94 mM), 50 µl of EuB2T2 txp (7.8 mM), and 100 µl of cytosine (0.423 mM), as internal standard, in 350 µl of 5.0 mM HEPES solution. The rate of UpU hydrolysis was monitored by removing 15 µl aliquots which were frozen until HPLC analysis was possible. All samples were microfiltered (0.2 µm) prior to injection on the HPLC. All runs were performed in triplicate. The background as determined from the simultaneous control containing no metal complex was negligible. The pseudo-zero order rate constant for the reaction was determined to be $k=(9.1\pm1.6)\times10^{-4}$ mM/h at 37° C., pH 7.0.

The pseudo-zero order rate constant for the hydrolytic cleavage of a ribodinucleotide by the nitrate salt of the water soluble EuB2T2 texaphyrin has been examined. Investigations indicate that a 0.15 mM aqueous solution of $Eu(B2T2 txph)^{2+}$ hydrolytically cleaved uridylyl (3'→5') uridine, UpU, (0.49 mM) with a pseudo-zero order rate of $(9.1\pm1.6)\times10^{-4}$ mM/h at 37° C., pH 7.0. In the absence of the metal complex no evidence of RNA cleavage was observed by HPLC. The reaction was followed by HPLC, monitoring the formation of uridine. Uridine-2'-monophosphate, uridine-3'-monophosphate, and uridine-2':3'-cyclicmonophosphate (cUMP) were also observed by HPLC; this indicates a hydrolytic rather than an oxidative mechanism for the cleavage reaction. Uridine-2':3'-cyclicmonophosphate reached a steady state concentration, implying that the texaphyrin complex hydrolyzed cUMP as well. Under identical conditions, a 0.15 mM aqueous solution of $Eu(NO_3)_3$ has a pseudo-zero order rate constant of $2.2\pm0.35)\times10^{-4}$ mM/h. Therefore, small traces of free metal ions cannot account for the hydrolysis observed in the presence of the texaphyrin metal complex. Under these conditions, the Eu(III) complex of HAM displayed a pseudo-zero order rate constant of $4.1\times10^{-4}$ mM/h. Thus, the texaphyrin complex is found to be more effective than the HAM system.

A survey of other lanthanide (III) complexes of the B2T2 texaphyrin indicates that these complexes are also capable of RNA hydrolysis. Results are summarized in Table 5.

TABLE 5

Rate Constants (Pseudo-Zero Order) for the Hydrolysis of UpU by Lanthanide (III) B2T2 Texaphyrin Complexes[a]

| LANTHANIDE CATION | k mM/h |
|---|---|
| La(III) | $1.16 \times 10^{-4}$ |
| Nd(III) | $4.69 \times 10^{-4}$ |
| Sm(III) | $6.3 \times 10^{-4}$ |
| Eu(III) | $4.99 \times 10^{-3}$ |
| Gd(III) | $1.44 \times 10^{-4}$ |
| Dy(III) | $6.0 \times 10^{-3}$ |
| Tm(III) | $4.16 \times 10^{-4}$ |
| Lu(III) | $1.91 \times 10^{-4}$ |

[a]The concentrations of the Lanthanide (III) B2T2 $txph(NO_3)_2$ are all approximately 0.25 mM.

Further evidence supporting the catalytic effect of the texaphyrin metal complex was obtained by monitoring the formation of uridine produced from the Eu(T2B2Txp)(II) catalyzed decomposition of uridine-2',3'-cyclicmonophosphate (cUMP). The decomposition of cUMP (0.10 mM) catalyzed by Eu(T2B2Txp)(II) (0.15 mM), when incubated at 37° C. and pH=7.0 (5 mM HEPES buffer), had a pseudo-zero order rate of $6.94\times10^{-5}$ $mMh^{-1}$ for the production of uridine. Examination of the reaction products by HPLC indicated that initially, cUMP is isomerized to uridine-3'-monophosphate (3'-UMP) and uridine-2'-monophosphate (2'-UMP) which are subsequently hydrolytically cleaved to produce uridine.

C. Generalized Hydrolysis of RNA Using a Texaphyrin Metal Complex

This section describes the use of europium texaphyrin in degrading a population of RNA molecules. $P^{32}$-labelled RNA transcripts from an isolated clone was the homogenous RNA substrate. The transcripts and their degradation products were visualized by polyacrylamide gel electrophoresis and autoradiography. Using the synthetic methodology of this invention, a polymer-supported europium texaphyrin would be created and used as described hereinbelow for the unsupported complex. It is contemplated that the polymer-supported version would function essentially as the free version, but with the significant added advantages associated with being attached to a column, e.g., the purification of the hydrolysed products.

pGEM®-3Z vector and Riboprobe® RNA transcript systems were obtained from Promega Corporation, Madison, Wis. A 4.3 kb fragment of the mouse 1b Multi Drug Resistant gene (MDR) was cloned into the EcoRI site of the pGem 3Z vector and its orientation determined. The plasmid was used in transcription reactions and when digested with BamHI, T7 RNA polymerase makes a transcript from this template that is approximately 2000 bases long. The transcription reaction consisted of 100 ng of BamHI digested pGem 3Z/4.3 MDR#3, 20 µl of 5× transcription buffer, triphosphate nucleotides (A,C,G) at 500 µM, UTP at 100 µM, 50 µC of $^{32}$-P α-UTP (3000 Ci/mmol), 10 mmol DTT, 120 units of RNasin and 70–100 units T7 RNA polymerase. This reaction was brought up to a total volume of 100 µl with DEPC treated double distilled water. The reaction was allowed to incubate at 37° C. for 1.5 hours. The entire reaction volume was then run over a G-50 Sephadex column (Nick column, Pharmacia) pre-equilibrated with 20 mM Tris pH 7.0, 2 mM EDTA, 0.1% SDS. The transcript was eluted from the column in the second 400 µl volume applied to the column. Any unincorporated nucleotide was left on the column.

Ten µl aliquots of the transcript were put into separate tubes and stock solutions of Eu(III)txp, EDTA or Eu(III)

acetate were added so that the final volume was 20 μl. The tubes were allowed to incubate for 2 hr at 37° C. Thirty μl of dye mix (formamide, 0.2% bromphenol blue) was added to each tube. The tubes were mixed and heated at 60° C., 5 min, then the entire content of the reaction was loaded Onto a 5% 8M urea polyacrylamide gel and electrophoresis was performed.

The results of the digests of the 2000 base long transcripts with EuB2T2 txp showed that there is one band in the control and control with EDTA. This band was absent in the lane with 100 μM EuB2T2 txp. An increase in lower molecular weight material, i.e. degradation products, was seen as smearing throughout. The transcript remains intact at the lower EuB2T2 txp concentrations. The transcript is degraded with 100 μM EuB2T2 txp in the presence of 500, 300, 100 and 10 μM amounts of EDTA. This study eliminates the possibility that free metal in the B2T2 txp solution is causing the degradation. The 100, 50, 25, 10 and 5 μM concentrations of free Europium metal salt (EuOAc) did not digest the transcript. These results are not affected by the presence of EDTA.

A digestion of total RNA (primarily 28s and 18s ribosomal RNA from K562 cells) with EuOAc, EuT2B2 txp and GdT2B2 txp indicated that all are able to hydrolyze total RNA. The digestions were performed in 50% DMSO and $H_2O$, the gel was electrophoresed using a 10 μM phosphate buffer, pH 6.8. It is likely that EuOAc digests the homogeneous transcript also but at higher EuOAc concentrations than those used in the present example.

Clearly, EuB2T2 texaphyrin is able to hydrolyze RNA substrates. Since the texaphyrins have such versatility for functionalization, this result has significant implications for the construction of site-specific cleaving reagents for nucleic acids.

D. Site-Specific Hydrolysis of RNA by Europium(III)-Texaphyrin Conjugated to a Synthetic Oligodeoxyribonucleotide The present section provides antisense agents using a texaphyrin metal complex-oligonucleotide conjugate that effects the hydrolysis of its RNA complement without the participation of endogenous nucleases. A DNA-EuTx-oligonucleotide conjugate was synthesized based on the functionalized texaphyrin. This "ribozyme analogue" provides an example of oligodeoxynucleotide-directed, metal catalyzed hydrolysis of a complementary RNA oligomer. Polymer-supported DNA-EuTx-oligonucleotide conjugates, created as described above, could be used as described for the unsupported complex. It is contemplated that the polymer-supported version would function essentially as the free version, but with all the advantages associated with being attached to a column, such as the purification of the hydrolysed products.

Two 20-mer oligonucleotides were machine-synthesized to contain alkylamine groups at either the 5-position of an internal thymine residue or the 5'-end terminal phosphate. Oligodeoxynucleotide-amines modified on the 5-position of thymine were purchased from Oligo's Etc. (Wilsonville, Oreg.); oligodeoxynucleotide-amines modified on the 5' end were purchased from Keystone Laboratories, Inc. (Menlo Park, Calif.). Oligonucleotides were HPLC purified and precipitated using LiCl prior to use. Reaction of the carboxylic acid functionalized europium(III) texaphyrin complex ($8_B$ of U.S. Ser. No. 08/227,370) with carbodiimide and N-hydroxysuccinimide produced the corresponding activated ester, which was added directly to a solution of the chosen oligodeoxynucleotide amine. The resulting DNA-EuTx conjugates were purified by electrophoresis.

A synthetic RNA 30-mer was obtained as substrate (Keystone Labs, Inc., Menlo Park, Calif.), with a sequence selected from a unique site within the gene transcript for multiple drug resistance. Sequence is complementary at 1562 bases post-transcriptional start site in mouse multidrug resistance protein mRNA. The 3'-$^{32}$P-labelled substrate was incubated with an excess of oligodeoxynucleotide conjugate at 37° C. for 18–24 h in a buffered salt solution, ethanol precipitated, and assayed on a 20% denaturing polyacrylamide gel. About 30% cleavage occurred near the expected location of the europium (III) texaphyrin complex upon hybridization with the conjugate. Cleavage yield was measured by densitometry and calculated as ratio of cleavage band to intact material. The corresponding cleavage bands were not observed when this same substrate was incubated with oligonucleotides that were non-complementary in sequence, unmodified, or were modified internally with the complex. Control reactions indicate that ambient light, calf thymus DNA or type of buffer (Tris acetate or HEPES, EDTA, pH 6.0–8.0) had no apparent effect on cleavage efficiency. EDTA inhibits cleavage by free lanthanide (III) cations.

The cleavage fragments co-migrate with bands in sequencing lanes produced by incubation of substrate under alkaline conditions or subjected to partial digestion with a series of base-specific ribonucleases. This observation is consistent with a hydrolytic mechanism, presumably involving the EuTx acting as a Lewis acid that facilitates an intramolecular attack of the 2'-hydroxyl group to effect cleavage. There are bands indicating site-specific cleavage of the ribonucleotide target sequence in the absence of any added cleavage reagents. Although the source of this background cleavage is unknown, it is believed to be the direct result of a higher order structure (i.e., a hairpin) of the oligoribonucleotide, since hybridization with any complementary oligonucleotide dramatically inhibits the cleavage. This type of structure-dependent cleavage behavior has been seen previously with oligoribonucleotides.

Maximal cleavage activity of the Eu(III)Txp-oligonucleotide was observed down to 25 nM conjugate. Decreased cleavage below this level may be due to a decrease in hybridized material (as judged by increased background cleavage of the target RNA present at a concentration of about 1 nM). By means of comparison, the free europium complex non-specifically hydrolyzed the RNA substrate at 25 μM. In the control reaction containing both complex and the non-derivatized complementary DNA oligomer, cleavage occurred predominantly in the single stranded region, although still at lower efficiency than the Eu-Tx-DNA conjugate at 2.5 nM. Thus, attachment of the EuTx to the DNA probe increases its effective concentration ca. 10,000-fold. A target RNA without the secondary structure observed here would likely allow for cleavage at lower DNA-EuTx concentrations. These data indicate the utility of such conjugates in specific cleavage applications.

As demonstrated in the present example, the selectivity of the texaphyrin complexes is enhanced by covalently linking oligonucleotides onto the periphery of the macrocycle. Since the metal complexes do cleave RNA over DNA preferentially, the DNA appendages would remain intact during the hydrolysis. The DNA arm will recognize and bind to an appropriate RNA segment, effectively increasing the metal concentration at these loci relative to the overall metal concentration in solution. Phosphate ester hydrolysis will therefore be significantly increased at specific locations along the RNA backbone. In one embodiment, primers (known or deduced) for PCR could be coupled to a hydrolytic divalent or trivalent texaphyrin complex to induce hydrolysis of proximal RNA or DNA.

Matrix-supported texaphyrin complexes that bind to complementary RNA or DNA sequences via an appended oligonucleotide could be employed to cleave RNA or DNA proximal to this specific site. Either one or two texaphyrin molecules may be attached to the DNA.

In light of the present disclosure, one skilled in the art will readily recognize that solid-supported catalysts can also be developed from the homogeneous hydrolysis catalysts described in each of the sections B through D. The advantages of the new solid-supported catalysts will include ease of separation of catalyst from substrate and product as well as the development of continuous flow processes.

E. Site-Specific Light-Dependent Cleavage of DNA by LuTxp-Oligonucleotide Conjugate The present section provides for the site-specific light-dependent cleavage of DNA by lutetium(III) texaphyrinoligonucleotide conjugate.

A reaction mixture was prepared by adding ca. 300,000 cpm of 5'-$^{32}$P-labeled DNA 36-mer (4 µL) to a solution made from lutetium(III) texaphyrin-oligonucleotide conjugate (2.5 µL, 407 nM stock solution, $R_8$ of the texaphyrin was NH—$(CH_2)_6$—$PO_4$— oligonucleotide), 4× buffer (5 µL) and water (8.5 µL) to produce a final volume of 20 µL. The oligonucleotide portion of the conjugate was complementary to a region of the DNA 36-mer. Final conjugate concentration was 50 nM. The 4× buffer is 400 mM NaCl, 200 mM HEPES, pH 7.5, 100 µM EDTA. Eight reaction mixtures were pipetted into O-ring type Eppendorf tubes (1.6 mL). Two additional reaction mixtures (tubes 1 and 6) were prepared in the same way, except that an equal volume of water was substituted for the LuTx-DNA conjugate. Tubes 1–5 were covered with an atmosphere of oxygen, and tubes 6–10 with an atmosphere of argon. Samples were sealed with parafilm, vortexed and centrifuged briefly, and then irradiated with laser light via the side of the Eppendorf tube. The laser was set at 752 nm and a power density of ca. 150 mW/cm$^2$ was used (ca. 20% reduction of laser power density is estimated to occur due to attenuation by the Eppendorf tube). Samples were irradiated for 1, 5, 10, or 30 minutes, whereupon the DNA was precipitated with ethanol using standard methods. The samples were resuspended in 50% formamide loading buffer, denatured at 90° C. for 5 minutes, and analyzed by electrophoresis on a 20% denaturing polyacrylamide gel.

Control reactions containing free lutetium(III) B2T2 texaphyrin were prepared by adding ca. 300,000 cpm of 5'-$^{32}$P-lableled DNA 36-mer (4 µL) to a solution made from lutetium(III) texaphyrin B2T2 (U.S. Pat. No. 5,252,720, incorporated by reference herein) (5 µL, 2 µM stock solution), 4× buffer (5 µL) and water (6 µL) to produce a final volume of 20 µL. Final LuB2T2Tx complex concentration was 500 nM. Eight reaction mixtures were pipetted into O-ring type Eppendorf tubes (1.6 mL). Two additional reaction mixtures (tubes 11 and 16) were prepared in the same way, except that an equal volume of water was substituted for the LuB2T2Tx solution. Tubes 11–15 were covered with an atmosphere of oxygen, and tubes 16–20 with an atmosphere of argon. Samples were irradiated, ethanol precipitated, and analyzed by electrophoresis as described above.

The resulting autoradiograph indicated substantial cleavage only in those lanes that contained the 12-mer LuTx-DNA conjugate. The cleavage sites covered four residues, proximal to the anticipated location of the LuTx-DNA conjugate. Both the locations of cleavage and the much greater efficiency of conjugate cleavage relative to that caused by free complex are consistent with a model whereby hybridization of the DNA increases the local concentration of the LuTx and effects site-specific cleavage.

The autoradiograph also contained information regarding cleavage mechanism: The presence of oxygen in reactions 2–5 clearly increased the efficiency of DNA strand breakage. That cleavage occurred at all in samples under argon is presumably attributable either to ambient light prior to the layering with argon, or else to incomplete replacement of the atmosphere in these tubes. The positive effect of oxygen on cleavage implicates singlet oxygen or other oxygen product as the intermediary species responsible for DNA strand breakage.

The maximal extent for cleavage observed was roughly 5% and was obtained after 5 minutes of laser irradiation. It is possible that the actual yield of reaction is far greater, since the initial step in cleavage is likely a nicking step and complete cleavage would be facilitated, for example, in vitro, by an organic base such as piperidine. Not wanting to be bound by theory, it is possible that singlet oxygen attacks a purine base, adenine for example, and causes depurination of double-stranded DNA similar to the Maxam and Gilbert chemical cleavage of DNA.

Further irradiation had no effect on the amount of cleavage. This observation is consistent with self-destruction of the 12-mer LuTx conjugate (which is also composed of DNA) or may reflect an instability of the LuTx complex towards laser light. The disappearance of low mobility material assigned as non-denatured DNA·LuTx conjugate duplex at greater laser irradiation times provides additional support for these possibilities.

F. Sequence-Specific Light-Dependent Cleavage of DNA by LuTxp Conjugated to 2'-O-Methyl RNA The present section provides for the site-specific light-dependent cleavage of DNA by lutetium(III) texaphyrin-2'-O-methyl RNA oligonucleotide conjugates.

Reaction mixtures were prepared by adding ca. 100,000 cpm of two different 5'-$^{32}$P-labeled DNA 36-mers (A, B) to solutions made from lutetium(III) texaphyrin oligonucleotide conjugate (O-Me oligonucleotide complementary to portion of A) (1.0 µL, 968 nM stock solution) or Lu(III) Txp-oligonucleotide conjugate (O-Me oligonucleotide complementary to portion of B) (3.0 µL, 335 nM stock solution), 4× buffer (5 µL) and water to produce a final volume of 20 µL. Final conjugate concentration was 50 nM. The 4× buffer is 400 mM NaCl, 200 mM HEPES, pH 7.5, 100 µM EDTA. Two conjugate-free controls (samples 1 and 8) were prepared by substituting water for conjugate solution. Samples 1, 4–8, and 11–14 were irradiated for 4.5 hours at 37° C. using a 75 watt incandescent light at ca. 9 inches above the heating block. Samples 2, 3, 9, and 10 were incubated without exposure to light at 37° C. The DNA was precipitated with ethanol using standard methods following incubation. Samples 6, 7, 13, and 14 were dissolved in 10% aqueous piperidine solution (50 µL), heated at 90° C. for 30 minutes, then freeze-dried. All samples were resuspended in 50% formamide loading buffer, denatured at 90° C. for 5' and analyzed by electrophoresis on a 20% denaturing polyacrylamide gel.

The resulting autoradiograph indicated substantial cleavage only in those lanes that contained the appropriate complementary 15-mer LuTxp 2'-O-methyl RNA conjugate. The cleavage sites covered three to four residues, proximal to the anticipated location of the LuTxp complex. These cleavages are consistent with a model whereby hybridization of the 2'-O-methyl-LuTxp conjugates to their complementary sequences of DNA increases the local concentration of the LuTxp and effects site-specific cleavage.

The autoradiograph also contained information regarding cleavage mechanism: Certain positions within the cleavage site are clearly more reactive to cleavage than others. Definitive identification of these more reactive bases awaits further experimentation, but are tentatively assigned to positions containing purine bases.

The maximal extent of cleavage observed was roughly 10%, and was obtained using a piperidine treatment of the light-exposed samples. The effect of this piperidine treatment is at least a 10-fold increase in cleavage products, indicating that initial DNA lesions formed by the photochemical reaction require base assistance to efficiently produce strand breaks. As the extent of light-induced cleavage in non-piperidine-treated lanes is far lower than that obtained using laser irradiation, it may be possible to observe an increase in the yield of cleavage products by using both laser and piperidine treatments.

A texaphyrin-oligonucleotide conjugate of a derivatized RNA such as the 2'-O-methyl RNA analog used herein may provide stability against self-cleavage. RNA is hydrolyzed by LuTxp, however, the 2'-O-Me RNA lacks a 2'-OH and, therefore, is stable to hydrolysis. Therefore, an RNA analog oligomer may be more stable than a DNA oligomer for the Txp-oligonucleotide conjugate. The synthesis of RNA analog-conjugates is the same as for Txp-DNA conjugates discussed previously herein. An RNA-analog conjugate may be complementary to an antisense or a sense strand of DNA and forms a triple helix in the process of binding to a double helix.

EXAMPLE 15

POLYMERIC TEXAPHYRINS

In any of the embodiments concerning matrix-supported texaphyrins, a polymeric texaphyrin itself may be employed as the texaphyrin species. This Example describes the generation of polymeric texaphyrins, as may be used as part of a polymer-supported construct, or indeed, in other embodiments in which their polymeric nature would be an advantage, such as those outlined below. Examples 9 and 10 of co-pending application, PCT publication WO 94/09003, are specifically incorporated herein by reference for the purposes of supplementing the present example in terms of describing the synthetic methodology underlying the generation of polymeric species of expanded porphyrins.

A variety of texaphyrin derivatives are obtainable via alkylation of the phenolic precursors prior to cyclization and metallation. Some of these derivatives can be treated as components in polymer forming reactions. For instance, a T2B1-type derivative may be elaborated synthetically to provide a diamine substituent that may be polymerized by condensation with any of a variety of activated diesters, such as that of terephthalic acid as follows.

Alternatively, a T2B2-type derivative could be elaborated to bear two monoamine substituents, that may then be polymerized in a similar fashion.

Addition polymers may also be prepared. Alkylation of phenolic precursors with allylic or polyene halides would, upon elaboration, produce texaphyrin derivatives having alkene or polyene substituents. These compounds would serve as components of addition polymerization-type reactions with other alkenes, dienes, or polyenes that may or may not contain a texaphyrin as follows.

The properties of the resulting polymeric materials will depend on the identity of the metal cation within the macrocycle, substituents on the macrocyclic rim, the identity of the copolymer, and the degree and type of polymerization. These properties in turn serve to define the application for which the polymer may be used. For example, a gadolinium(III) texaphyrin with water solubilizing substituents polymerized with a hydrophilic partner to form a copolymer with an average molecular weight of 10–20 kiloDalton is contemplated to serve as a useful

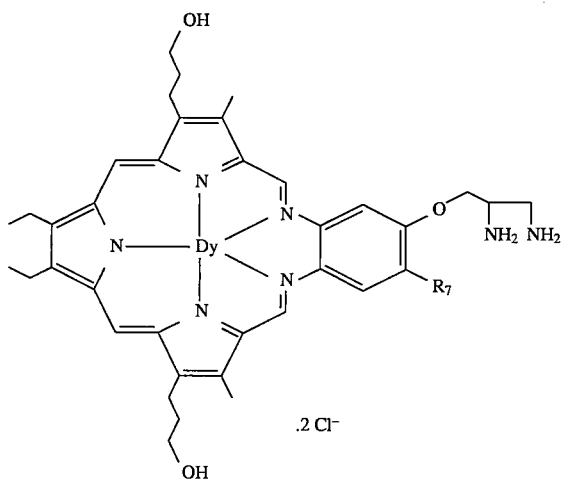

$R_7$ = OH, OCH$_2$CH$_2$OH, O(CH$_2$CH$_2$O)$_n$CH$_3$

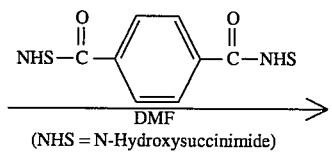

(NHS = N-Hydroxysuccinimide)

-continued
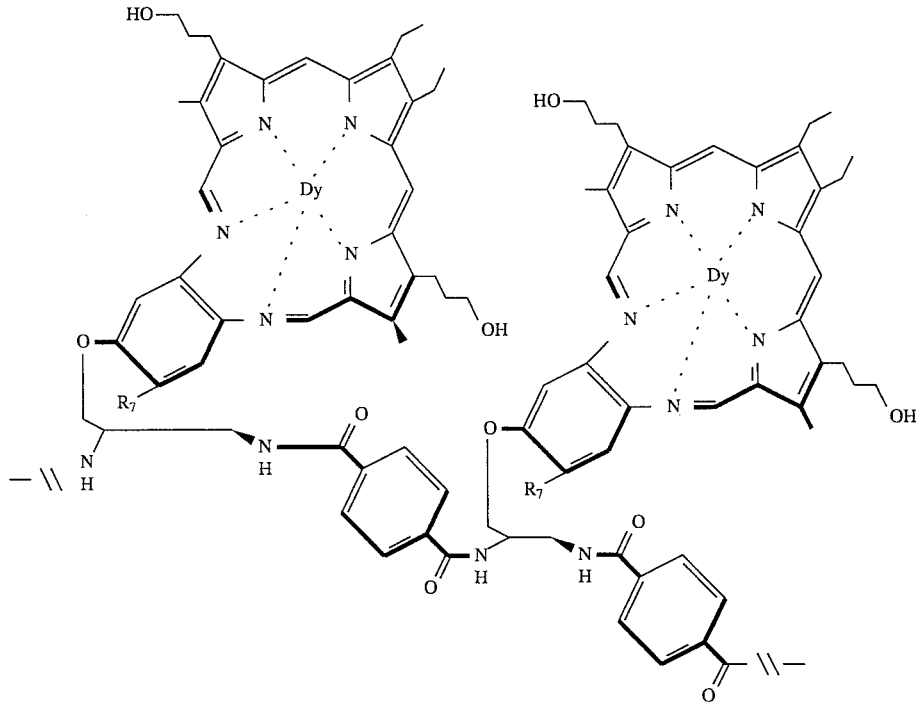
MRI blood pool agent. The size of the drug substance is expected to have an effect on its biodistribution and immunogenic properties: for instance, polymeric texaphyrin with 30 molecular
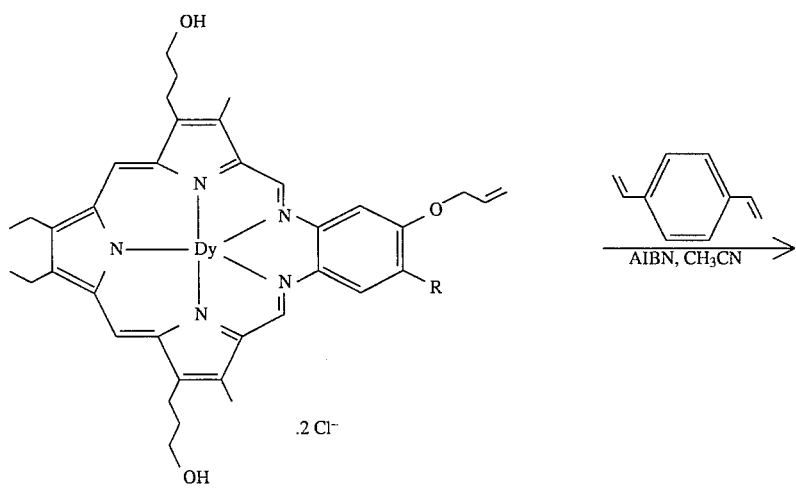
R7 = OH, OCH2CH2OH, O(CH2CH2O)nCH3

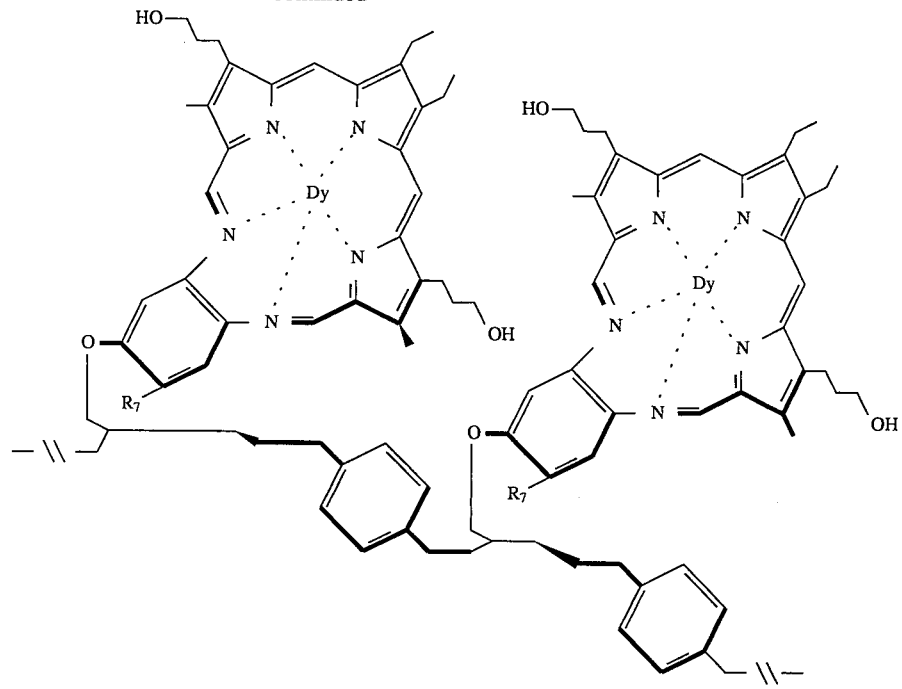
-continued weight above 10 kD should be recognized and removed by the lymphatic system in normal tissues, while the absence of a lymphatic system within tumors should allow the accumulation of the drug in these tissues (U.S. Pat. No. 4,649,151). These tumors may then be visualized by MRI, when Ln=Gd, or eradicated using PDT, when Ln=Lu. By polymerizing a drug substance it is also possible to reduce the osmotic load per given dose, thereby reducing its toxicity.

Alternatively, polymerization of more hydrophobic components is contemplated to produce materials suitable for molding and shaping. Wires drawn from such a material might find application in biological implants, such as catheters, which could be visualized by MRI. Such materials could also conceivably find application as semiconducting components, due to the organometallic nature of these materials, or linear optical devices.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention.

More specifically, it will be apparent that certain agents which are both chemically and physiologically related may be substituted for the agents described herein while the same or similar results would be achieved. For example, other large expanded porphyrins that bind anions are contemplated for use in similar embodiments to sapphyrins; and expanded porphyrins that contain a Lewis acid center are contemplated for use in catalytic hydrolysis, in a similar manner to the texaphyrins. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Sessler, J. L. et al., *Accounts of Chemical Research,* 1994, 27, 43.
2. (a) "Chemical and Enzymatic Synthesis of Gene Fragments: A Laboratory Manual"; H. G. Gassen and A. Lang, eds.; Verlag Chemie, Weinham, 1982. (b) "Oligonucleotide Synthesis: A Practical Approach"; M. J. Gait, ed.; IRL Press; Washington, D.C.; 1984.
3. Uhlman, E.; Peyman; *Chem. Rev.,* 1990, 90, 544.
4. Brown, P. R.; Roman, M.; *J. Chrom.,* 1992, 592, 3.
5. "HPLC in Biotechnology"; W. S. Hancock, ed.; J. Wiley & Sons: New York, 1990.
6. Frenz, J. et al.; *J. Chrom.,* 1993, 634, 229.
7. Chaiken, I. M. et al.; in "High Performance Liquid Chromatography"; J. Wiley; New York; 1989, pp 317–336.
8. "Rainin HPLC Instrumentation and Supplies Catalog", 1992–1992, 3.01–3.04.
9. Takemoto, K. et al.; *Poly. J.,* 1989, 21, 19–33.
10. (a) Fodora-Csorba, K. *J. Chrom.* 1992, 624, 353–367. (b) Grob, R. L. et al.; *J. Chrom. Sci.* 1993, 31, 183–191. (c) Grob, R. L. *J. Liq. Chrom.* 1993, 16, 1783–1802. (d) Gaind, A. K.; Loconto, P. R. *J. Chrom. Sci.* 1989, 27 569–573.
11. Sambrook, Fritsch, and Maniatis, *Molecular Cloning,* 2nd Edition, Cold Spring Harbor Laboratory Press, 1989.
12. Caracciolo et al. (1989) *Science,* 245:1107.
13. Sessler, J. L., et al., 1993, *Inorganic Chemistry,* 1993, 32, 3175–3187.

What is claimed is:

1. A composition comprising a matrix-supported texaphyrin.

2. The composition of claim 1 where the matrix is a polymericor solid-support matrix.

3. The composition of claim 1 wherein the texaphyrin is complexed to a metal cation.

4. The composition of claim 3, wherein the metal cation is La(III), Nd(III), Sm(III), Sm(II), Gd(III), Tm(III), Lu(III), Eu(III), Dy(III), Y(III), In(III), Ce(III), Sc(III), Ca(II), Mn(II), Ni(II), Zn(II), Cd(II), Hg(II), Mn(III), Co(II), Co(III), Ni(III), Fe(II), Fe(III), Cu(II), Ho(III), Pr(III), Tb(III), Er(III) or Yb(III).

5. The composition of claim 3, wherein the metal cation is Sm(III), Eu(III), Gd(III) or Dy(III).

6. The composition of claim 3, wherein the metal cation is La(III), Lu(III), or Y(III).

7. The composition of claim 1 wherein the texaphyrin is joined to the matrix by a linker XY, wherein X is [—(CH$_2$)$_n$—]—NH$_2$ where n is an integer from 0 to 20, OH, CO$_2$H, Cl, Br, I, OH, NCO, NCS, NC, C≡CH, CH=CH$_2$, MgCl, ZnCl, Li, a nucleotide or an oligonucleotide, and Y is [—(CH$_2$)$_n$—]—OH where n is an integer from 0 to 20, NH$_2$, CO$_2$H, Cl, Br, I, NCO, NCS, oxirane, C≡CH, MgCl, ZnCl, Li, a nucleotide or an oligonucleotide.

8. The composition of claim 1 wherein the texaphyrin is joined to the matrix by a linker XY, wherein X is [—(CH$_2$)$_n$—]—OH where n is an integer from 0 to 20, NH$_2$, CO$_2$H, Cl, Br, I, NCO, NCS, oxirane, C≡CH, MgCl, ZnCl, Li, a nucleotide or an oligonucleotide, and Y is [—(CH$_2$)$_n$—]—NH$_2$ where n is an integer from 0 to 20, OH, CO$_2$H, Cl, Br, I, OH, NCO, NCS, NC, C≡CH, CH=CH$_2$, MgCl, ZnCl, Li, a nucleotide or an oligonucleotide.

9. The composition of claim 1 wherein the texaphyrin is joined to the matrix by an ether, ester, amide, amine, carbamate, urea, —CH=CH—, —C≡C—, —(CH$_2$)$_m$— where m is an integer from 1 to 20, functionalized alkyl, aryl, or oligonucleotide linker.

10. The composition of claim 1 wherein the matrix is a solid-support matrix and the solid-support is silica, silica gel, amino-functionalized silica gel, alumina, clay, zeolite, glass, controlled pore glass or montmorillonite.

11. The composition of claim 1 wherein the matrix is silica gel.

12. The composition of claim 1 wherein the matrix is a polymer-support matrix and the polymer is polystyrene, polyethylene, polyacrylamide, polypropylene, polyamide, Merrifield resin, sepharose, agarose, polystyrene, polydivinylbenzene, cellulose, alginic acid, chitosan, chitin, polystyrene-benzhydrylamine resin, an acrylic ester polymer, a lactic acid polymer, a texaphyrin multimer or a sapphyrin multimer.

13. The composition of claim 1 wherein the matrix is polyurethane, polyvinylchloride, nylon, latex, silicone rubber, a halogenated polyethylene, an organosilicone, a biocompatible ceramic, bioglass or sintered hydroxyapatite.

14. The composition of claim 1 formulated into a column.

15. The composition of claim 1 formulated into a capillary electrophoresis tube.

16. The composition of claim 1 wherein the matrix-supported texaphyrin is in the form of a medical device.

17. The composition of claim 16, wherein the medical device is implantable.

18. The composition of claim 16, where the medical device is a catheter, an orthopedic implant, an artificial joint or a part thereof.

19. The composition of claim 1, wherein the texaphyrin further comprises a D-sugar unit, an L-sugar unit, an oligosaccharide, an L-amino acid, a D-amino acid, a peptide or a polypeptide.

20. The composition of claim 1, wherein the texaphyrin further comprises a nucleobase-containing group.

21. A method for separating a first molecule from a mixture of at least two molecules comprising the step of contacting a matrix-supported texaphyrin metal complex with said mixture to separate said first molecule.

22. The method of claim 21, wherein the metal is La(III), Nd(III), Sm(III), Sm(II), Gd(III), Tm(III), Lu(III), Eu(III), Dy(III), Y(III), In(III), Ce(III), Sc(III), Ca(II), Mn(II), Ni(II), Zn(II), Cd(II), Hg(II), Mn(III), Co(II), Co(III), Ni(III), Fe(II), Fe(III), Cu(II), Ho(III), Pr(III), Tb(III), Er(III) or Yb(III).

23. The method of claim 21, wherein the matrix-supported texaphyrin comprises a texaphyrin linked to a polymeric or solid-support matrix via an ether, ester, amide, amine, carbamate, urea, —CH=CH—, —C≡C—, —(CH$_2$)$_m$— where m is an integer from 1 to 20, functionalized alkyl, aryl, or oligonucleotide linker.

24. The method of claim 21, wherein the matrix-supported texaphyrin comprises a silica, silica gel, amino-functionalized silica gel, alumina, clay, zeolite, glass, controlled pore glass, montmorillonite, polystyrene, polyethylene, polyacrylamide, polypropylene, polyamide, Merrifield resin, sepharose, agarose, polystyrene, polydivinylbenzene, cellulose, alginic acid, chitosan, chitin, polystyrene-benzhydrylamine resin, an acrylic ester polymer, a lactic acid polymer, a texaphyrin multimer, a sapphyrin multimer, polyurethane, polyvinylchloride, nylon, latex, silicone rubber, a halogenated polyethylene, an organosilicone; or a biocompatible ceramic, bioglass or sintered hydroxyapatite polymeric or solid-support matrix.

25. The method of claim 21, wherein the matrix-supported texaphyrin is formulated into an HPLC column, a capillary electrophoresis tube or a filter cartridge.

26. The method of claim 21, wherein said mixture to be separated includes a molecule having a chloride, bromide, fluoride, pseudohalide, phosphate, phosphonate, phosphate ester, arsenate, arsenate ester, carboxylate, nitrate, sulfate, sulfonate or sugar moiety within its structure.

27. The method of claim 21, wherein said mixture to be separated includes a molecule having a phosphate, nitrate, organophosphorus or nucleotide moiety within its structure.

28. The method of claim 27, wherein said mixture to be separated includes an RNA or DNA molecule.

29. The method of claim 27, wherein said mixture includes a pesticide, an herbicide, a fungicide, or a chemical warfare agent.

30. A method for hydrolysing a phosphate ester, comprising the step of contacting a matrix-supported texaphyrin metal complex where the metal cation has catalytic activity for ester bond hydrolysis in aqueous solution with the phosphate ester to cleave the ester.

31. The method of claim 30, wherein the metal cation is Eu(III) or Dy(III).

32. The method of claim 30, wherein the phosphate ester is a nucleotide, an RNA molecule, a cofactor or a phospholipid.

33. The method of claim 32, wherein the phosphate ester is an RNA molecule.

34. A method of light-induced cleavage of a polymer of deoxyribonucleic acid, the method comprising:

contacting the polymer with a matrix-supported texaphyrin where the texaphyrin is a photosensitive texaphyrin; and exposing the matrix-supported texaphyrin to light for a time sufficient to cleave the polymer.

35. The method of claim 34 wherein the exposing step is carried out in the presence of oxygen.

36. The method of claim 34 wherein the photosensitive texaphyrin is a texaphyrin complexed with a diamagnetic metal and the diamagnetic metal is Lu(III), La(III), In(III), Zn(II) or Cd(II).

37. A method for conducting a chemical reaction catalyzed by a lanthanide metal cation comprising the step of contacting a matrix-supported texaphyrin complexed to a metal cation, where the metal cation is a lanthanide metal cation, with a composition comprising the substrates for the chemical reaction.

38. The method of claim 37, wherein the lanthanide metal cation is La(III), Sm(III), Gd(III), Y(III), Tb(III), Lu(III), Eu(III), Ce(III) or Dy(III).

39. The method of claim 37, wherein the chemical reaction is ester hydrolysis, amide hydrolysis, phosphate ester hydrolysis, acyl transfer, hydrogenation or polymerization.

40. A method of magnetic resonance imaging of a subject, comprising:

administering a matrix-supported texaphyrin complexed to a metal cation, wherein the metal cation is a paramagnetic metal cation, to the subject; and imaging the subject by reference to the matrix-supported texaphyrin.

41. A method of light-induced singlet oxygen production comprising subjecting a matrix-supported texaphyrin of claim 1 to light in the presence of oxygen.

42. A method of photodynamic tumor therapy comprising:

contacting a matrix-supported texaphyrin with a composition suspected of having tumor cells; and photoirradiating the matrix-supported texaphyrin in contact with the composition.

43. A method for deactivating a retrovirus or an enveloped virus comprising contacting a matrix-supported texaphyrin with a composition suspected of having a retrovirus or enveloped virus; and photoirradiating the matrix-supported texaphyrin in contact with the composition.

44. The composition of claim 2 where the matrix is a polymeric matrix and the polymeric matrix is a texaphyrin multimer.

* * * * *

UNITED STATES PATENT AND TRADEMARK OFFICE
CERTIFICATE OF CORRECTION

PATENT NO.   :   5,594,136

DATED        :   January 14, 1997

INVENTOR(S)  :   Sessler et al.

It is certified that error appears in the above-identified patent and that said Letters Patent is hereby corrected as shown below:

In claim 2, column 60, line 65, please delete "polymericor" and insert -- polymeric or -- therefor.

Signed and Sealed this

Twentieth Day of May, 1997

Attest:

BRUCE LEHMAN

Attesting Officer

Commissioner of Patents and Trademarks